(12) United States Patent
Vogels et al.

(10) Patent No.: US 7,816,104 B2
(45) Date of Patent: Oct. 19, 2010

(54) PACKAGING CELLS FOR RECOMBINANT ADENOVIRUS

(75) Inventors: Ronald Vogels, Linschoten (NL); Menzo Jans Emco Havenga, Alphen aan den Rijn (NL); David Adrianus Theodorus Maria Zuijdgeest, The Hague (NL)

(73) Assignee: Crucell Holland B.V., Leiden (NL)

( * ) Notice: Subject to any disclaimer, the term of this patent is extended or adjusted under 35 U.S.C. 154(b) by 795 days.

(21) Appl. No.: 11/384,850

(22) Filed: Mar. 20, 2006

(65) Prior Publication Data

US 2006/0183232 A1    Aug. 17, 2006

Related U.S. Application Data

(63) Continuation of application No. PCT/EP2004/052428, filed on Oct. 4, 2004.

(30) Foreign Application Priority Data

Oct. 2, 2003    (WO) .................. PCT/EP03/50679

(51) Int. Cl.
C12P 19/34    (2006.01)
C12N 7/00    (2006.01)
A61K 48/00    (2006.01)

(52) U.S. Cl. .................. 435/91.4; 435/235.1; 435/6; 435/325; 514/44; 424/93.1

(58) Field of Classification Search .................. None
See application file for complete search history.

(56) References Cited

U.S. PATENT DOCUMENTS

| | | | |
|---|---|---|---|
| 4,889,806 A * | 12/1989 | Olson et al. .................. 435/91.53 |
| 5,610,053 A | 3/1997 | Chung et al. |
| 5,686,279 A | 11/1997 | Finer et al. |
| 5,994,128 A | 11/1999 | Fallaux et al. |
| 6,379,944 B1 | 4/2002 | Mittal et al. |
| 6,558,948 B1 | 5/2003 | Kochanek et al. |
| 7,026,164 B2 * | 4/2006 | Li et al. .................. 435/455 |
| 7,074,618 B2 | 7/2006 | Li et al. |
| 7,132,284 B2 | 11/2006 | Li et al. |
| 2007/0141706 A1 | 6/2007 | Li et al. |

FOREIGN PATENT DOCUMENTS

| | | |
|---|---|---|
| WO | WO 95 34671 | 12/1995 |
| WO | WO 96/17053 | 6/1996 |
| WO | WO 96/18418 | 6/1996 |
| WO | WO 00/63403 | 10/2000 |
| WO | WO 01/38362 A2 | 5/2001 |
| WO | WO 02/40665 A2 | 5/2002 |
| WO | WO 03/004704 A2 | 1/2003 |
| WO | WO 03/031633 A2 | 4/2003 |
| WO | WO 2005/010146 A2 | 2/2005 |
| WO | WO 2005/033320 A1 | 4/2005 |

OTHER PUBLICATIONS

Fallaux et al., New Helper Cells and Matched Early Region 1-Deleted Adenovirus Vectors Prevent Generation of Replication-Competent Adenoviruses, Human Gene Therapy, Sep. 1, 1998, pp. 1909-1917, vol. 9.
Gallimore et al., Transformation of Human Embryo Retinoblasts with Simian Virus 40, Adenovirus and *ras* Oncogenes, Anticancer Research, 1986, pp. 499-508, vol. 6.
Imler et al., Novel complementation cell lines derived from human lung carcinoma A549 cells support the growth of E1-deleted adenovirus vectors, Gene Therapy, 1996, pp. 75-84, vol. 3.
Jochemsen et al., Activation of adenovirus 5 E1A transcription by region E1B in transformed primary rat cells, The EMBO Journal, 1987, pp. 3399-3405, vol. 6, No. 11.
Lochmuller et al., Emergence of Early Region 1-Containing Replication-Competent Adenovirus in Stocks of Replication-Defective Adenovirus Recombinants (deltaE1 + deltaE3) During Multiple Passages in 293 Cells, Human Gene Therapy, Dec. 1994, pp. 1485-1491, vol. 5.
Murakami et al., A Single Short Stretch of Homology Between Adenoviral Vector and Packaging Cell Line Can Give Rise to Cytopathic Effect-Inducing, Helper-Dependent E1-Positive Particles, May 20, 2002, pp. 909-920, vol. 13.
Van Den Elsen et al., The relationship between region E1a and E1b of human adenoviruses in cell transformation, Gene, 1982, pp. 175-185, vol. 18.
PCT International Preliminary Examination Report, PCT/EP2004/052428, dated Oct. 11, 2005.
PCT International Search Report, PCT/EP2004/052428, dated Feb. 18, 2005.
NCBI accession No. gi:56160529 as accessed on Oct. 13, 2008.

* cited by examiner

*Primary Examiner*—J D Schultz
(74) *Attorney, Agent, or Firm*—TraskBritt

(57) ABSTRACT

In the absence of substantial sequence overlap between a recombinant adenoviral vector and the genome of a packaging cell, helper-dependent E1-containing particles (HDEP) can be formed at low frequency. The invention provides means and methods reducing or preventing the generation of HDEP. To this purpose, novel packaging cells and methods of making these are provided.

18 Claims, 22 Drawing Sheets

SEQUENCE LISTING

```
<160> NUMBER OF SEQ ID NOS: 18

<210> SEQ ID NO 1
<211> LENGTH: 7315
<212> TYPE: DNA
<213> ORGANISM: Artificial
<220> FEATURE:
<221> NAME/KEY: human phosphoglycerate kinase promoter
<222> LOCATION: (17)..(504)
<220> FEATURE:
<221> NAME/KEY: E1 region of human adenovirus type 5 genome
<222> LOCATION: (513)..(3564)
<220> FEATURE:
<221> NAME/KEY: hepatitis B virus polyadenylation sequence
<222> LOCATION: (3588)..(4205)
<220> FEATURE:
<223> OTHER INFORMATION: plasmid pIG.E1A.E1B

<400> SEQUENCE: 1
gaattcgata attccacggg gttggggttg cgccttttcc aaggcagccc tgggtttgcg     60
cagggacgcg gctgctctgg gcgtggttcc gggaaacgca gcggcgccga ccctgggtct    120
cgcacattct tcacgtccgt tcgcagcgtc acccggatct tcgccgctac ccttgtgggc    180 ccccccggcga cgcttcctgc tccgcccta agtcgggaag gttccttgcg gttcgcggcg    240
tgccggacgt gacaaacgga agccgcacgt ctcactagta ccctcgcaga cggacagcgc    300
cagggagcaa tggcagcgcg ccgaccgcga tgggctgtgg ccaatagcgg ctgctcagca    360
gggcgcgccg agagcagcgg ccgggaaggg gcggtgcggg aggcggggtg tggggcggta    420
gtgtgggccc tgttcctgcc cgcgcggtgt tccgcattct gcaagcctcc ggagcgcacg    480
tcggcagtcg gctccctcgt tccgaattcg atcgtgtagt gtatttatac ccggtgagtt    540
cctcaagagg ccactcttga gtgccagcga gtagagtttt ctcctccgag ccgctccgac    600
accgggactg aaaatgagac atattatctg ccacggaggt gttattaccg aagaaatggc    660
```

```
cgccagtctt ttggaccagc tgatcgaaga ggtactggct gataatcttc cacctcctag    720
ccattttgaa ccacctaccc ttcacgaact gtatgattta gacgtgacgg cccccgaaga    780
tcccaacgag gaggcggttt cgcagatttt tcccgactct gtaatgttgg cggtgcagga    840
agggattgac ttactcactt ttccgccggc gcccggttct ccggagccgc ctcacctttc    900
ccggcagccc gagcagccgg agcagagagc cttgggtccg gtttctatgc caaaccttgt    960
accggaggtg atcgatctta cctgccacga ggctggcttt ccacccagtg acgacgagga   1020
tgaagagggt gaggagtttg tgttagatta tgtggagcac cccgggcacg gttgcaggtc   1080
ttgtcattat caccggagga atacggggga cccagatatt atgtgttcgc tttgctatat   1140
gaggacctgt ggcatgtttg tctacagtaa gtgaaaatta tgggcagtgg gtgatagagt   1200
ggtgggtttg tgtggtaat tttttttta attttacag ttttgtggtt taaagaattt   1260
tgtattgtga tttttttaaa aggtcctgtg tctgaacctg agcctgagcc cgagccagaa   1320
ccggagcctg caagacctac ccgccgtcct aaaatggcgc tgctatcct gagacgcccg   1380 acatcacctg tgtctagaga atgcaatagt agtacggata gctgtgactc cggtccttct   1440
aacacacctc ctgagataca cccggtggtc ccgctgtgcc ccattaaacc agttgccgtg   1500
agagttggtg ggcgtcgcca ggctgtggaa tgtatcgagg acttgcttaa cgagcctggg   1560
caacctttgg acttgagctg taaacgcccc aggccataag gtgtaaacct gtgattgcgt   1620
gtgtggttaa cgcctttgtt tgctgaatga gttgatgtaa gtttaataaa gggtgagata   1680
atgtttaact tgcatggcgt gttaaatggg gcggggctta aagggtatat aatgcgccgt   1740
gggctaatct tggttacatc tgacctcatg gaggcttggg agtgtttgga agattttttct   1800 gctgtgcgta acttgctgga acagagtctct aacagtacct cttggttttg gaggtttctg   1860
tggggctcat cccaggcaaa gttagtctgc agaattaagg aggattacaa gtgggaattt   1920
gaagagcttt tgaaatcctg tggtgagctg tttgattctt tgaatctggg tcaccaggcg   1980
cttttccaag agaaggtcat caagactttg gatttttcca caccggggcg cgctgcggct   2040
gctgttgctt ttttgagttt tataaaggat aaatggagcg aagaaaccca tctgagcggg   2100
gggtacctgc tggattttct ggccatgcat ctgtggagag cggttgtgag acacaagaat   2160
cgcctgctac tgttgtcttc cgtccgcccg gcgataatac cgacggagga gcagcagcag   2220
cagcaggagg aagccaggcg gcggcggcag gagcagagcc catggaaccc gagagccggc   2280
ctggaccctc gggaatgaat gttgtacagg tggctgaact gtatccagaa ctgagacgca   2340
ttttgacaat tacagaggat gggcagggc taaagggggt aaagagggag cgggggcttt   2400
gtgaggctac agaggaggct aggaatctag ctttagctt aatgaccaga caccgtcctg   2460
agtgtattac ttttcaacag atcaaggata attgcgctaa tgagcttgat ctgctggcgc   2520
agaagtattc catagagcag ctgaccactt actggctgca gccaggggat gattttgagg   2580
aggctattag ggtatatgca aaggtggcac ttaggccaga ttgcaagtac aagatcagca   2640
aacttgtaaa tatcaggaat tgttgctaca tttctgggaa cggggccgag gtggagatag   2700
atacggagga tagggtggcc tttagatgta gcatgataaa tatgtggccg ggggtgcttg   2760
gcatggacgg ggtggttatt atgaatgtaa ggtttactgg ccccaatttt agcggtacgg   2820
ttttcctggc caataccaac cttatcctac acggtaag cttctatggg tttaacaata   2880
cctgtgtgga agcctggacc gatgtaaggg ttcggggctg tgccttttac tgctgctgga   2940
agggggtggt gtgtcgcccc aaaagcaggg cttcaattaa gaaatgcctc tttgaaaggt   3000
gtaccttggg tatcctgtct gagggtaact ccagggtgcg ccacaatgtg gcctccgact   3060
```

```
gtggttgctt catgctagtg aaaagcgtgg ctgtgattaa gcataacatg gtatgtggca      3120
actgcgagga cagggcctct cagatgctga cctgctcgga cggcaactgt cacctgctga      3180
agaccattca cgtagccagc cactctcgca aggcctggcc agtgtttgag cataacatac      3240
tgacccgctg ttccttgcat ttgggtaaca ggaggggggt gttcctacct taccaatgca      3300
atttgagtca cactaagata ttgcttgagc ccgagagcat gtccaaggtg aacctgaacg      3360
gggtgtttga catgaccatg aagatctgga aggtgctgag gtacgatgag acccgcacca      3420
ggtgcagacc ctgcgagtgt ggcggtaaac atattaggaa ccagcctgtg atgctggatg      3480
tgaccgagga gctgaggccc gatcacttgg tgctggcctg cacccgcgct gagtttggct      3540
ctagcgatga agatacagat tgagctcgac ctgcaggcat gcaagctgat ccttcgcggg      3600
acgtcctttg tttacgtccc gtcggcgctg aatcccgcgg acgacccctc gcggggccgc      3660
ttgggactct ctcgtcccct tctccgtctg ccgttccagc cgaccacggg gcgcacctct      3720
ctttacgcgg tctccccgtc tgtgccttct catctgccgg tccgtgtgca cttcgcttca      3780
cctctgcacg ttgcatggag accaccgtga acgcccatca gatcctgccc aaggtcttac      3840
ataagaggac tcttggactc ccagcaatgt caacgaccga ccttgaggcc tacttcaaag      3900
actgtgtgtt taaggactgg gaggagctgg gggaggagat taggttaaag gtctttgtat      3960
taggaggctg taggcataaa ttggtctgcg caccagcact atgcaacttt ttcacctctg      4020
cctaatcatc tcttgtacat gtcccactgt tcaagcctcc aagctgtgcc ttgggtggct      4080
ttggggcatg gacattgacc cttataaaga atttggagct actgtggagt tactctcgtt      4140
tttgccttct gacttctttc cttccgtcag agatcctgca gagcttggtg aaggcagtg       4200
gaattagctt ggcgtaatca tggtcatagc tgtttcctgt gtgaaattgt tatccgctca      4260
caattccaca caacatacga gccggaagca taaagtgtaa agcctggggt gcctaatgag      4320
tgagctaact cacattaatt gcgttgcgct cactgcccgc tttccagtcg ggaaacctgt      4380
cgtgccagct gcattaatga atcggccaac gcgcgggag aggcggtttg cgtattgggc       4440
gctcttccgc ttcctcgctc actgactcgc tgcgctcggt cgttcggctg cggcgagcgg      4500
tatcagctca ctcaaaggcg gtaatacggt tatccacaga atcagggat aacgcaggaa        4560
agaacatgtg agcaaaaggc cagcaaaagg ccaggaaccg taaaaaggcc gcgttgctgg      4620
cgtttttcca taggctccgc cccctgacg agcatcacaa aaatcgacgc tcaagtcaga       4680
ggtggcgaaa cccgacagga ctataaagat accaggcgtt tccccctgga agctccctcg      4740
tgcgctctcc tgttccgacc ctgccgctta ccggatacct gtccgccttt ctcccttcgg      4800
gaagcgtggc gctttctcat agctcacgct gtaggtatct cagttcggtg taggtcgttc      4860
gctccaagct gggctgtgtg cacgaacccc ccgttcagcc cgaccgctgc gccttatccg      4920
gtaactatcg tcttgagtcc aacccggtaa gacacgactt atcgccactg gcagcagcca      4980
ctggtaacag gattagcaga gcgaggtatg taggcggtgc tacagagttc ttgaagtggt      5040
ggcctaacta cggctacact agaaggacag tatttggtat ctgcgctctg ctgaagccag      5100
ttaccttcgg aaaaagagtt ggtagctctt gatccggcaa acaaaccacc gctggtagcg      5160
gtggtttttt tgtttgcaag cagcagatta cgcgcagaaa aaaaggatct caagaagatc      5220
ctttgatctt ttctacgggg tctgacgctc agtggaacga aaactcacgt taagggattt      5280
tggtcatgag attatcaaaa aggatcttca cctagatcct tttaaattaa aaatgaagtt      5340
ttaaatcaat ctaaagtata tatgagtaaa cttggtctga cagttaccaa tgcttaatca      5400
```

-continued

```
gtgaggcacc tatctcagcg atctgtctat ttcgttcatc catagttgcc tgactccccg      5460
tcgtgtagat aactacgata cgggagggct taccatctgg ccccagtgct gcaatgatac      5520
cgcgagaccc acgctcaccg gctccagatt tatcagcaat aaaccagcca gccggaaggg      5580
ccgagcgcag aagtggtcct gcaactttat ccgcctccat ccagtctatt aattgttgcc      5640
gggaagctag agtaagtagt tcgccagtta atagtttgcg caacgttgtt gccattgcta      5700
caggcatcgt ggtgtcacgc tcgtcgtttg gtatggcttc attcagctcc ggttcccaac      5760
gatcaaggcg agttacatga tcccccatgt tgtgcaaaaa agcggttagc tccttcggtc      5820
ctccgatcgt tgtcagaagt aagttggccg cagtgttatc actcatggtt atggcagcac      5880
tgcataattc tcttactgtc atgccatccg taagatgctt ttctgtgact ggtgagtact      5940
caaccaagtc attctgagaa tagtgtatgc ggcgaccgag ttgctcttgc ccggcgtcaa      6000
tacgggataa taccgcgcca catagcagaa ctttaaaagt gctcatcatt ggaaaacgtt      6060
cttcggggcg aaaactctca aggatcttac cgctgttgag atccagttcg atgtaaccca      6120
ctcgtgcacc caactgatct tcagcatctt ttactttcac cagcgtttct gggtgagcaa      6180
aaacaggaag gcaaaatgcc gcaaaaaagg aataagggc gacacggaaa tgttgaatac      6240
tcatactctt cctttttcaa tattattgaa gcatttatca gggttattgt ctcatgagcg      6300
gatacatatt tgaatgtatt tagaaaaata aacaaatagg ggttccgcgc acatttcccc      6360
gaaaagtgcc acctgacgtc taagaaacca ttattatcat gacattaacc tataaaaata      6420
ggcgtatcac gaggcccttt cgtctcgcgc gtttcggtga tgacggtgaa aacctctgac      6480
acatgcagct cccggagacg gtcacagctt gtctgtaagc ggatgccggg agcagacaag      6540
cccgtcaggg cgcgtcagcg ggtgttggcg ggtgtcgggg ctggcttaac tatgcggcat      6600
cagagcagat tgtactgaga gtgcaccata aaattgtaaa cgttaatatt tgttaaaat      6660 tcgcgttaaa ttttttgttaa atcagctcat tttttaacca ataggccgaa atcggcaaaa      6720
tcccttataa atcaaaagaa tagcccgaga tagggttgag tgttgttcca gtttggaaca      6780
agagtccact attaaagaac gtggactcca acgtcaaagg gcgaaaaacc gtctatcagg      6840
gcgatggccc actacgtgaa ccatcaccca aatcaagttt ttttggggtcg aggtgccgta      6900 aagcactaaa tcggaaccct aaagggagcc cccgatttag agcttgacgg ggaaagccgg      6960
cgaacgtggc gagaaaggaa gggaagaaag cgaaaggagc gggcgctagg gcgctggcaa      7020
gtgtagcggt cacgctgcgc gtaaccacca cacccgccgc gcttaatgcg ccgctacagg      7080
gcgcgtacta tggttgcttt gacgtatgcg gtgtgaaata ccgcacagat gcgtaaggag      7140
aaaataccgc atcaggcgcc attcgccatt caggctgcgc aactgttggg aagggcgatc      7200
ggtgcgggcc tcttcgctat tacgccagct ggcgaaaggg ggatgtgctg caaggcgatt      7260
aagttgggta acgccagggt ttcccagtc acgacgttgt aaaacgacgg ccagt            7315
```

<210> SEQ ID NO 2
<211> LENGTH: 26
<212> TYPE: DNA
<213> ORGANISM: Artificial
<220> FEATURE:
<223> OTHER INFORMATION: primer 5E1Bfor-1

<400> SEQUENCE: 2
cggaattcgg cgtgttaaat ggggcg        26

<210> SEQ ID NO 3
<211> LENGTH: 20

<212> TYPE: DNA
<213> ORGANISM: Artificial
<220> FEATURE:
<223> OTHER INFORMATION: primer 5E1B-rev

<400> SEQUENCE: 3
tagcaggcga ttcttgtgtc                                              20

<210> SEQ ID NO 4
<211> LENGTH: 20
<212> TYPE: DNA
<213> ORGANISM: Artificial
<220> FEATURE:
<223> OTHER INFORMATION: primer 5E1A-For

<400> SEQUENCE: 4
ccgaattcga tcgtgtagtg                                              20

<210> SEQ ID NO 5
<211> LENGTH: 27
<212> TYPE: DNA
<213> ORGANISM: Artificial
<220> FEATURE:
<223> OTHER INFORMATION: primer 5E1A-rev

<400> SEQUENCE: 5
cgggatccat ttaacacgcc atgcaag                                      27

<210> SEQ ID NO 6
<211> LENGTH: 26
<212> TYPE: DNA
<213> ORGANISM: Artificial
<220> FEATURE:
<223> OTHER INFORMATION: primer 5E1AB21-rev

<400> SEQUENCE: 6
cgggatcctc attcccgagg gtccag                                       26

<210> SEQ ID NO 7
<211> LENGTH: 16
<212> TYPE: DNA
<213> ORGANISM: Artificial
<220> FEATURE:
<223> OTHER INFORMATION: oligonucleotide X-SM-1

<400> SEQUENCE: 7
ctaggtcgac caattg                                                  16

<210> SEQ ID NO 8
<211> LENGTH: 16
<212> TYPE: DNA
<213> ORGANISM: Artificial
<220> FEATURE:
<223> OTHER INFORMATION: oligonucleotide X-SM-2

<400> SEQUENCE: 8
ctagcaattg gtcgac                                                  16

<210> SEQ ID NO 9
<211> LENGTH: 44
<212> TYPE: DNA
<213> ORGANISM: Artificial
<220> FEATURE:
<223> OTHER INFORMATION: oligonucleotide EcoPst-3

<400> SEQUENCE: 9

```
aattgatatc gaattcgccg agctcgtaag cttggatccc tgca          44
```

<210> SEQ ID NO 10
<211> LENGTH: 36
<212> TYPE: DNA
<213> ORGANISM: Artificial
<220> FEATURE:
<223> OTHER INFORMATION: oligonucleotide EcoPst-4

<400> SEQUENCE: 10

```
gggatccaag cttacgagct cggcgaattc gatatc                  36
```

<210> SEQ ID NO 11
<211> LENGTH: 33
<212> TYPE: DNA
<213> ORGANISM: Artificial
<220> FEATURE:
<223> OTHER INFORMATION: primer COL1A2F

<400> SEQUENCE: 11

```
cagctagcct gcaggaagta tgcagattat ttg                     33
```

<210> SEQ ID NO 12
<211> LENGTH: 25
<212> TYPE: DNA
<213> ORGANISM: Artificial
<220> FEATURE:
<223> OTHER INFORMATION: primer COL1A2R-sal

<400> SEQUENCE: 12

```
acacgtcgac ggctggtaga gatgc                              25
```

<210> SEQ ID NO 13
<211> LENGTH: 36
<212> TYPE: DNA
<213> ORGANISM: Artificial
<220> FEATURE:
<223> OTHER INFORMATION: primer 55KforE

<400> SEQUENCE: 13

```
ggaattcgcc accatggagc gaagaaaccc atctga                  36
```

<210> SEQ ID NO 14
<211> LENGTH: 33
<212> TYPE: DNA
<213> ORGANISM: Artificial
<220> FEATURE:
<223> OTHER INFORMATION: primer 55KrevB

<400> SEQUENCE: 14

```
ggatcctcaa tctgtatctt catcgctaga gcc                     33
```

<210> SEQ ID NO 15
<211> LENGTH: 23
<212> TYPE: DNA
<213> ORGANISM: Artificial
<220> FEATURE:
<223> OTHER INFORMATION: primer 5E1Bstart

<400> SEQUENCE: 15

```
ggaattcctc atggaggctt ggg                                23
```

<210> SEQ ID NO 16
<211> LENGTH: 19
<212> TYPE: DNA
<213> ORGANISM: Artificial

```
<220> FEATURE:
<223> OTHER INFORMATION: primer 5E1Brev2

<400> SEQUENCE: 16
gtgtctcaca accgctctc                                                        19

<210> SEQ ID NO 17
<211> LENGTH: 33
<212> TYPE: DNA
<213> ORGANISM: Artificial
<220> FEATURE:
<223> OTHER INFORMATION: primer SV40.forS

<400> SEQUENCE: 17
caactagtac atgtggaatg tgtgtcagtt agg                                        33

<210> SEQ ID NO 18
<211> LENGTH: 28
<212> TYPE: DNA
<213> ORGANISM: Artificial
<220> FEATURE:
<223> OTHER INFORMATION: primer SV40.RevERI

<400> SEQUENCE: 18
ggaattcagc tttttgcaaa agcctagg                                              28
```

US 7,816,104 B2

PACKAGING CELLS FOR RECOMBINANT ADENOVIRUS

CROSS-REFERENCE TO RELATED APPLICATIONS

This application is a continuation of PCT International Patent Application No. PCT/EP2004/052428, filed on Oct. 4, 2004, designating the United States of America, and published, in English, as PCT International Publication No. WO 2005/033320 A1 on Apr. 14, 2005, which PCT International Patent Application claims priority under the Paris Convention and the Patent Cooperation Treaty to PCT International Patent Application No. PCT/EP03/50679, filed on Oct. 2, 2003, the contents of the entirety of each of which are hereby incorporated herein by this reference.

TECHNICAL FIELD

The invention relates to the field of biotechnology and molecular and cell biology; more in particular, to packaging cells and use thereof for the generation of batches of recombinant adenovirus.

BACKGROUND

Replication-deficient recombinant adenoviruses are useful, for instance, in gene therapy and for vaccination purposes. They usually lack the E1-region of an adenovirus and are, therefore, propagated on complementing cells providing the E1 sequences. The packaging cells provide all information required for replication of a vector that is packaged in the cells to form recombinant viral particles. An example of a packaging cell is a 293 cell, which contains nucleotides 1-4344 of the adenovirus 5 genome (Louis et al., 1997), which include the 5' inverted terminal repeat (ITR), the packaging signal, the E1A and E1B coding sequences and the pIX coding sequences.

Overlap between the adenoviral sequences in the packaging cell and the vector may lead to homologous recombination between these sequences, resulting in the generation of replication-competent adenovirus (RCA) (Lochmuller et al., 1994). This problem has been solved by using a packaging system consisting of a cell line and a vector that are matched to each other by lacking such overlapping sequences (Fallaux et al., 1998; U.S. Pat. No. 5,994,128). One example of a particularly useful cell line in such applications is the PER.C6® cell line (U.S. Pat. No. 5,994,128; Nichols et al., 2002).

Recently, it was reported that upon use of PER.C6® cells in conjunction with a vector that still contained 177 bp sequence homology with the E1 sequences in the genome of PER.C6®, a single cross-over event could result in the generation of helper-dependent replication-competent virus at a low frequency (Murakami et al., 2002). The generated atypical RCA was termed "helper-dependent E1-containing particle" (HDEP). As expected, the emergence of this type of particle was circumvented when a vector was used that lacked the sequence overlap with the E1 sequences in the genome of PER.C6® cells (Murakami et al., 2002).

However, it now unexpectedly appears that using the system of matched vector and PER.C6® cells, some batches of recombinant adenovirus are contaminated at a very low frequency with particles that can cause cytopathological effect (CPE) in cells lacking E1 sequences. The particle is helper-dependent and contains E1-sequences and, therefore, is also an HDEP. This HDEP is generated in the absence of substantial homology between vector and packaging cell (see Murakami et al., 2004).

While RCA is recognized by the regulatory authorities as a potential problem and detection of RCA in batches for clinical use is mandatory (USDHHS, FDA, CBER. Guidance for Industry, Guidance for human somatic cell therapy and gene therapy, March 1998), the safety aspects of HDEP are unclear. HDEP is replication deficient since it lacks the necessary viral genes for autonomous replication and, therefore, HDEP will not disseminate in a host. The theoretical possibility that the presence of a recombinant vector or wild-type adenovirus in the same cell may cause rescue and spread of HDEP cannot, however, be completely excluded. Hence, at least a latent need exists for means and methods for preventing generation of E1-containing particles during the preparation of batches of recombinant adenovirus particles. To this purpose, the present invention provides new cell lines, methods for preparing new cell lines, and the use thereof to make batches of RCA-free and HDEP-free recombinant adenovirus vectors.

SUMMARY OF THE INVENTION

Described herein are methods of generating a packaging cell comprising adenoviral E1A and E1B sequences, wherein E1A and at least one of the E1B coding regions are separated from each other in the genome of the cell. To this purpose, at least three embodiments are provided.

In a first embodiment, E1A and E1B can be introduced into a precursor cell at different moments in time, reducing the chance that E1A and E1B are co-integrated on the same chromosomal location.

In a second embodiment, the chances of co-integration into the same locus are reduced by introducing E1A and E1B coding sequences into a precursor cell on two different molecules that lack overlapping sequences that could otherwise lead to homologous recombination between these sequences.

In a third embodiment, E1A and at least one of the E1B coding regions are introduced by virtue of one nucleic acid molecule whereon these sequences are separated by a given distance. It will be clear that in the third embodiment, instead of a single nucleic acid molecule, two or more nucleic acid molecules can also be introduced, which would satisfy the criterion that the E1A and at least one of the E1B coding regions are separated by a given distance, in case these two or more molecules would form one molecule, e.g., by ligation, recombination, and the like. The resulting packaging cells are characterized in that E1A and both E1B coding regions are present at a distance from each other and, hence, the chances are reduced of E1A and both E1B coding sequences together being incorporated into the genome of a recombinant adenovirus that is propagated on such packaging cells.

The invention provides a method of preparing a cell capable of complementing E1-deficient adenoviral vectors without generating helper-dependent E1-containing particles, comprising the steps of: a) introducing into a precursor or ancestor of the cell nucleic acid sequence(s) coding for E1A gene functions and E1B gene functions, or if the precursor cell already comprises one of E1A or E1B gene functions, the other of the E1A and E1B gene functions; and b) selecting or identifying cells having obtained E1A and E1B in a chromosomal configuration that prevents the formation of helper-dependent E1-containing particles when the cells are used to complement a recombinant adenoviral vector deficient for one or more E1 gene functions, the vector lacking nucleic acid sequences that have substantial overlap with the chromosomally located E1 sequence that otherwise could give rise to homologous recombination.

In one aspect, the invention provides a method of preparing a cell having adenovirus E1A and E1B-19K and E1B-55K coding sequences in its genome, wherein nucleic acid sequences comprising those sequences are introduced into a precursor cell, the method characterized in that: a) at least two nucleic acid molecules together comprising those sequences are introduced into the precursor cell, wherein E1A and at least one of the E1B coding sequences are present on different nucleic acid molecules, which are introduced into the precursor cell on a different moment in time, and wherein the precursor cell is not a baby rat kidney cell; or b) a nucleic acid molecule comprising the E1A coding sequence and a nucleic acid molecule comprising the E1B coding sequences are introduced into the precursor cell, wherein the nucleic acid molecules lack substantial overlap that could otherwise lead to homologous recombination between the at least two molecules; or c) the nucleic acid sequences comprising E1A and at least one of the E1B coding sequences are separated by at least 4 kb on a single nucleic acid molecule or on two or more nucleic acid molecules when these would form a single nucleic acid molecule. Preferably, in embodiment c), the sequences are separated by at least 10 kb, more preferably at least 34.5 kb or more. Preferably, the separating sequences are non-E1 sequences so that integration of both expression cassettes of E1A and E1B together in a single virus genome is rendered very unlikely or impossible. Alternatively, when the E1A and at least one of the E1B sequences are separated by 0 to 15 kb, a screen for the absence of inverted repeats of the E1-sequences in the generated cells may be used to select for cells, wherein the possibility of generating HDEP upon propagation of recombinant adenovirus in the generated cells is decreased or absent. The invention also provides cells obtainable by the method according to the invention. The invention further provides a cell comprising adenovirus E1A and E1B-55K and E1B-19K coding sequences in its genome, characterized in that the cell lacks stretches of nucleic acid sequence, wherein E1A and both E1B coding sequences are separated by less than 4 kb in the genome. Preferably, the cell lacks stretches of nucleic acid sequence, wherein E1A and both E1B coding sequences are separated by less than 10 kb in the genome, more preferably, the cell lacks stretches of nucleic acid sequence, wherein E1A and both E1B coding sequences are separated by less than 34.5 kb in the genome.

It is another aspect of the invention to provide a method for providing or generating a cell comprising adenoviral E1 sequences, wherein E1 sequences include E1A and E1B coding sequences, characterized in that the method includes a step of selecting cells lacking inverted repeats comprising E1 sequences. The invention further provides a cell comprising adenovirus E1 sequences in its genome, wherein the E1 sequences include E1A and E1B coding sequences, characterized in that the E1 sequences are not present in the form of inverted repeats in the genome. In one embodiment thereof, the cell comprises at least two copies of the adenovirus sequences in its genome, which copies may be on the same chromosome. In another embodiment thereof, the cell comprises one copy of the E1 sequences in its genome, and further lacks sequences in its genome encoding (functional) pIX of an adenovirus.

It is another aspect of the invention to provide a method for generating a batch of recombinant adenovirus having a deletion in the E1 region, comprising the steps of: a) introducing the recombinant adenovirus into a cell comprising E1 sequences of an adenovirus capable of complementing the deleted E1 sequences of the recombinant adenovirus; b) culturing the cell and harvesting the recombinant adenovirus, the method characterized in that the cell is a cell according to the invention. It will be clear to the person skilled in the art that instead of introducing the recombinant adenovirus, it is also possible to start the generation of recombinant adenovirus by using one or more nucleic acid fragments capable of forming the genome of the recombinant adenovirus and which will, after replication and packaging in that cell, form the recombinant adenovirus. Hence, for this embodiment, a recombinant adenovirus may also be a genome of the recombinant adenovirus. In a preferred embodiment, the recombinant adenovirus lacks substantial sequence overlap with the E1 sequences present in the cell, which could otherwise lead to homologous recombination. In yet another embodiment, the invention provides a packaging system comprising a packaging cell comprising E1 sequences in its genome and a recombinant adenovirus vector with a deletion in the E1 region, wherein the genome of the vector lacks substantial overlap with the E1 sequences in the genome of the packaging cell, characterized in that the packaging cell is a cell according to the present invention.

Figure 1:
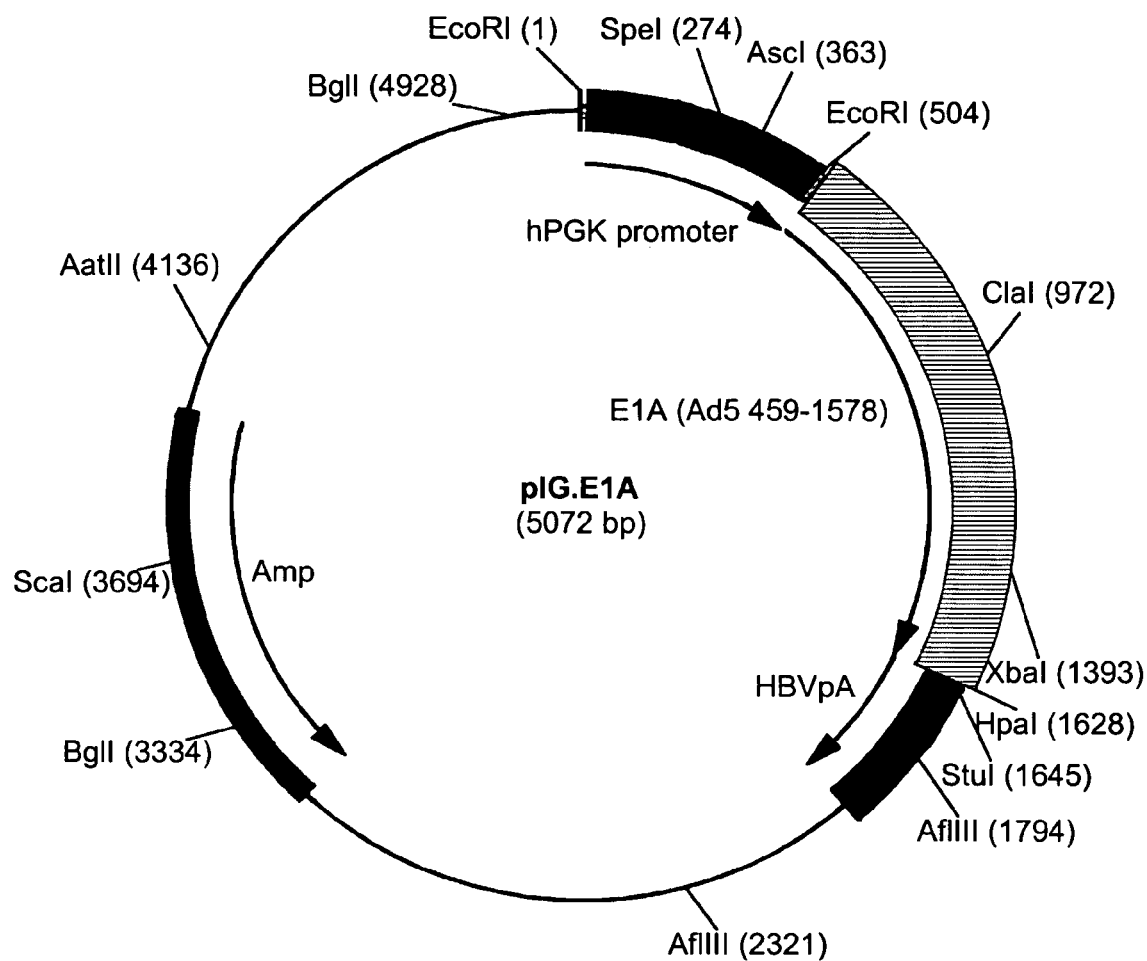
FIG. 1 is a map of pIG.E1A.

Lane A shows the natural configuration of the E1-region of the adenovirus genome: E1A is followed by E1B, which consists of E1B-19K and E1B-55K. No spacer sequence is present between E1A and E1B. Packaging cells of the prior art have been constructed by introducing DNA in this configuration and, hence, also have the E1 region in this configuration in their genome.

Lane B illustrates the two simplest of the possible configurations according to the present invention where a spacer (or stuffer) is present in the E1 region. Lane 1 shows a stuffer introduced between E1A and E1B-19K. Lane 2 shows a stuffer introduced between E1B-19K and E1B-55K. The rationale is to increase the distance between E1A, E1B-19K and E1B-55K compared to the natural situation, to decrease the possibility or prevent altogether the simultaneous uptake of these three open reading frames into a single adenovirus particle (prevent RCA and HDEP). The stuffer should be at least 4 kb to obtain a cell line according to the invention, the cell comprising adenovirus E1A and E1B-55K and E1B-19K coding sequences in its genome, characterized in that the cell lacks stretches of nucleic acid sequence, wherein E1A and both E1B coding sequences are separated by less than 4 kb in the genome. The order of the open reading frames does not matter as long as they are all present in the genome in a way that there is expression of E1A, E1B-19K and E1B-55K. Hence, the order may be E1A-E1B/19k-E1B/55k, E1B/19k-E1B/55k-E1A, E1B/55k-E1B/19k-E1A, E1B/55k-E1A-E1B/19k or E1B19k-E1A-E1B55k. When the E1B/19k and the E1B/55k are adjacent, they may be present as a single transcription unit or as separate transcription units. This is not critical to the invention. Both configurations (1 and 2) will be able to generate cell lines that fulfill this spacing criterion of the invention. Stuffer lengths of at least 6, 8, 10, 15 or 34.5 kb can generate cells according to the invention having all three open reading frames but lacking stretches of nucleic acid sequence, wherein E1A and both E1B coding sequences are separated by less than 6, 8, 10, 15 or 34.5 kb in their genome. This means that when a single fragment containing E1A+E1B-19K+E1B-55K together should come from the genome of the generated cells, this fragment should at least be 7 kb (stuffer 4 kb), 9 kb (stuffer 6 kb), etc., until at least 37.5 kb (stuffer of 34.5 kb), in contrast to the situation in A, where these sequences can be found in a fragment of only 3 kb of the genome of packaging cells generated with such constructs (E1A+E1B-19K+E1B-55K open reading frames together comprise about 3 kb).

Lane C is an extension of the principle illustrated in Lane B. Since the fragments as shown in Lane B could integrate adjacent to each other, a stuffer is also placed before E1A and/or after E1B in preferred embodiments of the invention (prevents close proximity of E1B of first repeat to E1A of second repeat). The genome of a resulting packaging cell is shown, wherein two copies of the E1 region provided with stuffer DNA are shown when integrated adjacent to each other in tandem repeat. These packaging cells of the invention have integrated in their genome E1A and E1B-19K and E1B-55K, but do not contain stretches of nucleic acid in their genome, wherein E1A and both E1B coding sequences are separated by less than 4 kb, etc., depending on the stuffer lengths (in this example, should be at least 4 kb between E1A and E1B-19K (No. 1) or between E1B-19K and E1B-55K (No. 2), and at least 2 kb upstream of E1A and 2 kb downstream of E1B-55K (together, 4 kb when integrated directly adjacent)).

DETAILED DESCRIPTION OF THE INVENTION

A replication-competent adenovirus (RCA) is an adenoviral particle that is capable of replication in cells without the need for helper adenovirus. An "HDEP" (helper-dependent E1-containing particle) as used herein is defined as a viral particle comprising at least E1A and E1B-55K coding sequences from an adenovirus, the particle not being able to replicate in a cell lacking functional E1A and/or E1B-55K in the absence of "helper virus." A helper virus may be wild-type or mutant adenovirus or any adenoviral vector providing the functions missing in HDEP and can, therefore, be provided by the (E1-defective) desired product recombinant adenovirus propagated on the packaging cell. The E1A and E1B 55K sequences are required for propagation of an adenovirus. The HDEP usually further contains E1B-19K coding sequences. The E1 sequences present in HDEP should be able to complement the recombinant E1-defective adenovirus, which can serve as a helper virus for HDEP.

HDEP can be generated by homologous recombination on overlap between the E1 sequences in a packaging cell and a vector (Murakami et al., 2002), but as now unexpectedly appears from several studies, it can also be generated in the absence of substantial homology/overlap between sequences in the packaging cell and vector, i.e., by a process referred to herein as non-homologous recombination (see, e.g., Murakami et al., 2004, for possible structures of HDEP). "Substantial overlap" as used herein is, therefore, defined as sufficient overlap for homologous recombination. In any case, in embodiments where the invention refers to "absence of substantial overlap," this condition is considered to be fulfilled if an overlap exists of no more than 50 nucleotides ("nt"), preferably less than 40 nt, more preferably less than 30 nt, still more preferably less than 20 nt, even still more preferably less than 10 nt, and most preferably no overlap at all.

Although the mechanism of the formation of HDEP is not fully understood at present, it is clear that the E1 sequences therein originate from the genome of the packaging cell. The presence of E1 sequences in recombinant adenovirus batches is unwanted, being in the form of RCA or HDEP. The invention provides methods and means that minimize the chance of generating HDEP. Thereto, methods for preparing cells and the resulting cells are provided, wherein the cells have E1A and E1B in a chromosomal configuration that prevents the introduction of E1A and E1B coding sequences together into a recombinant adenovirus and, hence, the formation of HDEP when the cells are used for the complementation of E1-deficient recombinant adenoviral vectors, in the absence of substantial sequence overlap between the vector and the chromosomally located E1 sequences of the complementing cells of the invention. To this purpose, the chromosomal conformation of the cells according to one embodiment of the invention is such that E1A and at least one of the E1B coding regions are separated in the genome of the novel cells. Since inverted repeats are believed to contribute to the formation of HDEP by stimulating the deletion of adenovirus sequences, in another embodiment, the invention provides cells comprising E1A and E1B coding sequences, wherein the E1 sequences are not present in inverted repeat conformation in the genome of the packaging cells.

The cells of the invention comprise adenovirus E1A and E1B coding sequences in their genome and preferably, they comprise the coding sequences for all functional E1A and both E1B (E1B-55K and E1B-19K) proteins in their genome. E1A and at least one of the E1B proteins may be of the same or optionally be of different serotype according to the invention.

Preferably in these embodiments, at least one of E1A and E1B are regulated by a promoter different from an E1A and E1B promoter, respectively.

Cells of the Invention

Figure 22:
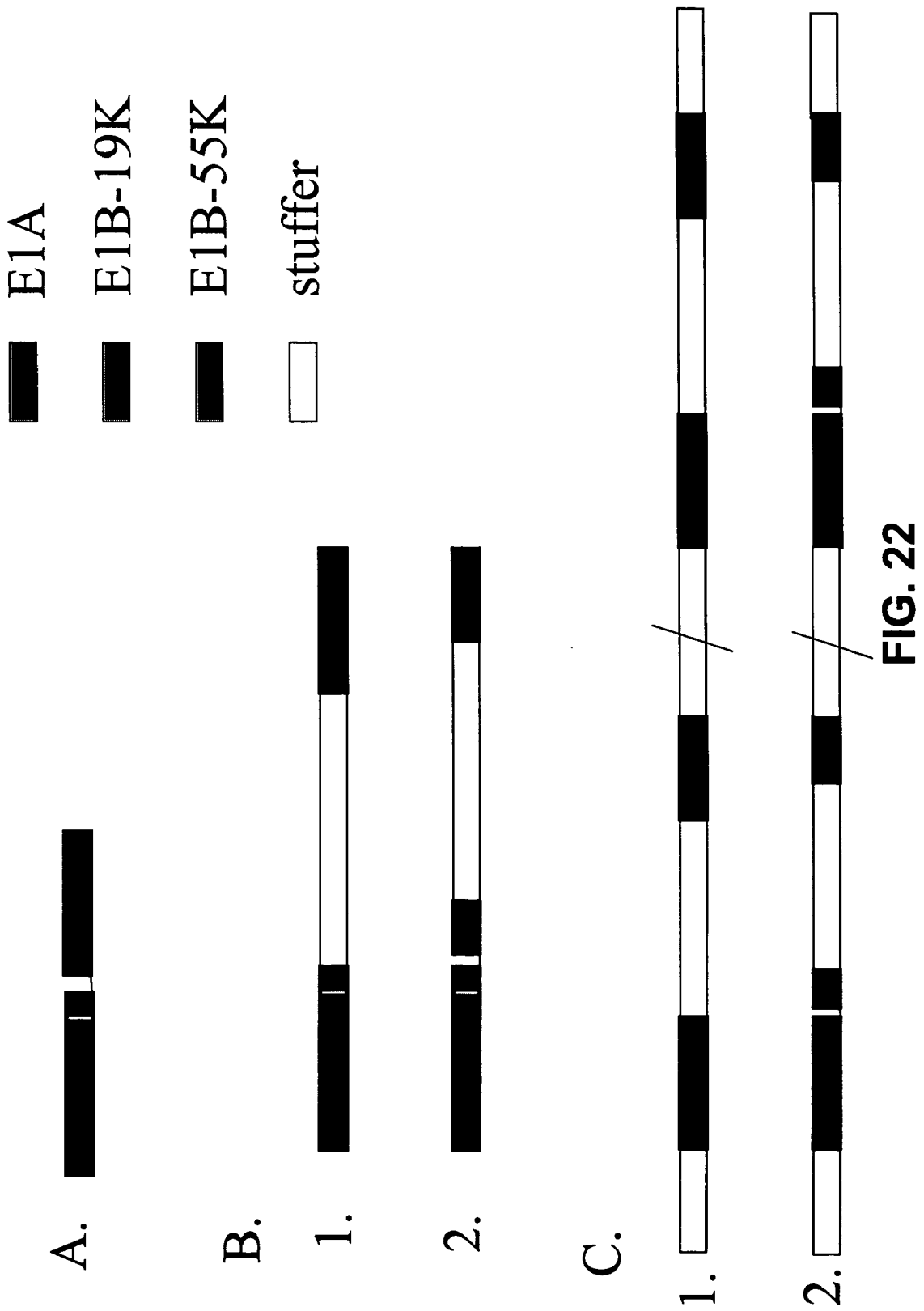
FIG. 22 depicts a schematic presentation of some embodiments of the invention (not to scale). Regulating sequences (such as promoters and polyA signals) are not depicted.

A recombinant adenovirus may be able to take up >20 kb of DNA from the cell line in which it is propagated, and the maximum genome length of an adenovirus allowing efficient packaging is approximately 38 kb (for an adenovirus type 5-based vector; this figure may depend somewhat on the serotype). This feature is used to prepare novel complementing cells according to the invention, the cells comprising E1A and E1B coding sequences, and the cells characterized in that E1A and at least one of the E1B sequences are separated by at least 4 kb, preferably at least 10 kb, and more preferably at least 34.5 kb in the genome. This means that the genome of such cells lacks stretches of nucleic acid sequence wherein E1A and both E1B coding sequences are separated by less than 4, 10 or 34.5 kb, respectively (see, e.g., FIG. 22 for a schematic representation). It will be clear that wherever the present invention mentions that two sequences are separated by at least a given distance in a genome of a cell, this requirement is deemed to be fulfilled as well when the two sequences are present on separate chromosomes. Hence, the embodiment where the two sequences are on different chromosomes is expressly included within the meaning "at least x kb apart" or "separated by at least x kb" in the genome, as used herein. Such an embodiment can be easily checked by methods known to the person skilled in the art, for example, by fluorescent in situ hybridization (FISH), which can be used to locate the chromosome and/or chromosome location where a given sequence is present.

The cells of the invention comprise adenovirus sequences in their genome and preferably, those adenovirus sequences encode all E1 proteins but lack sequences encoding pIX, or a part thereof (i.e., such cells preferably do not contain sequences from the open reading frame of pIX; for cells with Ad5 E1 sequences, this means that they preferably do not contain nt 3609-4031 of wt Ad5 or parts thereof), and more preferably, they also have deletions in the pIX promoter (for cells with Ad5 E1 sequence, preferably no sequences of the pIX promoter downstream from nt 3550, more preferably 3525) in order to prevent significant overlap with adenovirus vectors having pIX under control of its own promoter. The absence of pIX sequences from the genome of the packaging cells aids in preventing overlap between the genome and a recombinant adenovirus vector (U.S. Pat. No. 5,994,128, the contents of which are incorporated by this reference).

The cells according to the invention may be derived from immortalized cells such as A549, Hela and the like, in which case a selection marker is required to establish the cells. Preferably, the cells according to the invention are derived from primary cells, in which case, selection is provided by the E1A and E1B transforming activity (see examples). In preferred aspects, the cells are derived from retina cells. They may be cells of any origin, including of human origin. For the propagation of human adenovirus, cells of human origin are preferred. The cells may, for instance, also be of bovine origin for the propagation of recombinant bovine adenovirus (U.S. Pat. No. 6,379,944). The origin of the cells may be chosen by the person skilled in the art to be compatible with the recombinant adenovirus of choice.

In one aspect, the cells are derived from primary human retina cells (also referred to as HER cells). Immortalization of such cells with adenoviral E1 sequences has, for instance, been described in U.S. Pat. No. 5,994,128, in Byrd et al., 1982, 1988, and Gallimore et al., 1986. Primary HER cells can be isolated from fetuses (Byrd et al., 1982, 1988). In other embodiments, the cells are derived from primary human embryonic kidney cells (see, e.g., Graham et al., 1977). In yet other embodiments, the cells are derived from primary amniocytes, such as human primary amniocytes (see, e.g., U.S. Pat. No. 6,558,948 for methods of immortalizing primary amniocytes with adenovirus E1 sequences).

Generation of Cells

The cells according to the invention can be generated by introducing adenovirus E1A and E1B-55K and E1B-19K coding sequences into a precursor or ancestor cell (hence, the cells are derived from the precursor or ancestor cell by introduction of the E1 sequences therein). According to the invention, E1A and at least one of the E1B coding sequences are to be introduced into the precursor cells in an unlinked manner. "Unlinked" as used in this connotation, is meant to refer to a configuration that is different from the natural configuration of E1A and E1B as found in an adenovirus, i.e., directly adjacent to each other (see, e.g., FIG. 14 where the natural, i.e., "linked," configuration of E1A and E1B is shown as present in plasmid pIG.E1A.E1B).

It is to be noted that prior to the present invention, the person skilled in the art that wished to obtain a packaging cell comprising in its genome adenovirus E1A and both E1B coding sequences, would not contemplate introducing E1A and at least one E1B sequence in an unlinked manner, because: a) it is more work and hence less convenient, and b) both E1A and E1B sequences are required for immortalization. Previous studies, that were done to gain insight into the transforming capabilities of E1A and E1B proteins, have demonstrated that introduction of E1A and at least one E1B coding sequence can lead to established clones (van den Elsen et al., 1982; Gallimore et al., 1986; Jochemsen et al., 1987; Rao et al., 1992; Nevels et al., 2001). However, the simultaneous introduction of these plasmids, and/or the overlap between the introduced sequences, e.g., in the plasmid sequences, the regulatory sequences such as promoter and/or polyadenylation signal, and the E1B-55K and E1B-19K overlapping sequence likely results in the co-integration of E1A and both E1B coding regions in the same locus in the genome. Indeed such co-integration was observed by van den Elsen et al. (1982). In one case (Jochemsen et al., 1987), baby rat kidney (BRK) cells were first transfected with E1A and picked clones were then transfected with an E1B plasmid to study the influence of E1B expression on E1A expression. Obviously, this study was done on a specific type of cells and for a reason unrelated to the invention described in this application.

Prior to the present invention, there was no reason to separately transfect E1A and at least one of the E1B coding sequences for the purpose of generating a packaging cell. The formation of HDEP in the absence of substantial overlap between the genome of the recombinant adenovirus and the packaging cell was hitherto not described. Furthermore, the person skilled in the art would, in fact, be dissuaded to use this method for obtaining other than BRK-derived cells, such as, for instance, human cells, since Gallimore et al. (1986) had described that human cells were only rarely morphologically transformed by expressing E1A only and most clones died in situ or immediately after isolation. The sole case where an Ad12 (subgroup A) E1A-expressing plasmid resulted in a clone was identified 114 days post-transfection and could only be picked after the clone had overgrown the dish. Clearly, the person skilled in the art would not be motivated to introduce E1A and at least one E1B gene into precursor cells on a separate moment in time based on the prior art. It is the merit of the present invention to provide such methods for obtaining cells that have E1A and at least one E1B coding sequence separated in their genome.

In certain aspects, the cells of the present invention are preferably not baby rat kidney (BRK) cells. In one preferred aspect, the cells of the invention are human cells. In a preferred aspect, the cells are derived from HER cells. It will be clear that the cells wherein the E1 sequences are introduced according to the present invention, before introducing, are preferably free from adenovirus E1A and E1B coding sequences in their genome and, only upon introduction of the sequences, will obtain the E1 sequences in their genome, thereby becoming immortalized and capable of packaging recombinant adenovirus with deletions in the E1 region. For instance, WO 03/031633 describes the introduction of Ad11 E1B-55k into 293 cells: this will clearly not lead to the advantages of the present invention, since the E1 sequences as already present in 293 remain in the original configuration and will have an E1B ORF less than 4 kb apart from the E1A ORF. In contrast, the present invention provides methods for generating cells having adenovirus E1A and E1B-19K and E1B-55K coding sequences in their genome, as well as the resulting cells from the methods, whereby the nucleic acid sequences comprising E1A and at least one of the E1B coding sequences are sufficiently separated from each other to prevent the simultaneous introduction of all E1A and E1B sequences from the genome of the cells into the genome of a single adenovirus particle.

According to a first embodiment for generating the cells of the present invention, the E1A and at least one of the E1B coding sequences are separately introduced into the precursor cell, by placing them on separate molecules that are introduced into the cell on a different moment in time, and the precursor cells are not BRK cells. In one embodiment hereof, first the E1A and E1B-21K coding sequences are introduced, while the E1B-55K coding sequence is introduced at a later moment in time.

According to a second embodiment for generating the cells of the present invention, at least two nucleic acid molecules together comprising E1A and E1B coding sequences are introduced into the precursor cell, characterized in that at least two nucleic acid molecules lack substantial overlapping sequences. It is believed that the presence of such overlapping sequences would enhance the possibility of at least some way of interaction between at least two molecules and the subsequent co-integration of the sequences on the molecules into the same locus of the genome of the precursor cell into which the molecules are introduced, whereas it is an object of the present invention to circumvent this. In one embodiment hereof, at least one of the E1A and E1B coding regions are placed under control of different heterologous regulatory sequences, such as promoters and polyadenylation sequences. In another embodiment hereof, the E1B-55K and E1B-19K sequences, which are overlapping, are separated and all overlap between these coding sequences is removed by genetic engineering using knowledge of the redundancy of the genetic code, according to methods known to the person skilled in the art, thereby allowing the introduction of these E1B coding sequences independently and unlinked from each other. Introduction of the E1A and E1B coding regions in this embodiment may be at the same time, for instance, by co-transfection of at least two molecules, but obviously, the first and second embodiments may also be combined, i.e., introduction of at least two molecules comprising nucleic acid sequences together comprising E1A and both E1B coding sequences, wherein at least two molecules lack substantial overlap with respect to each other, and wherein at least two molecules are introduced into a precursor cell on a different moment in time.

Figure 13:
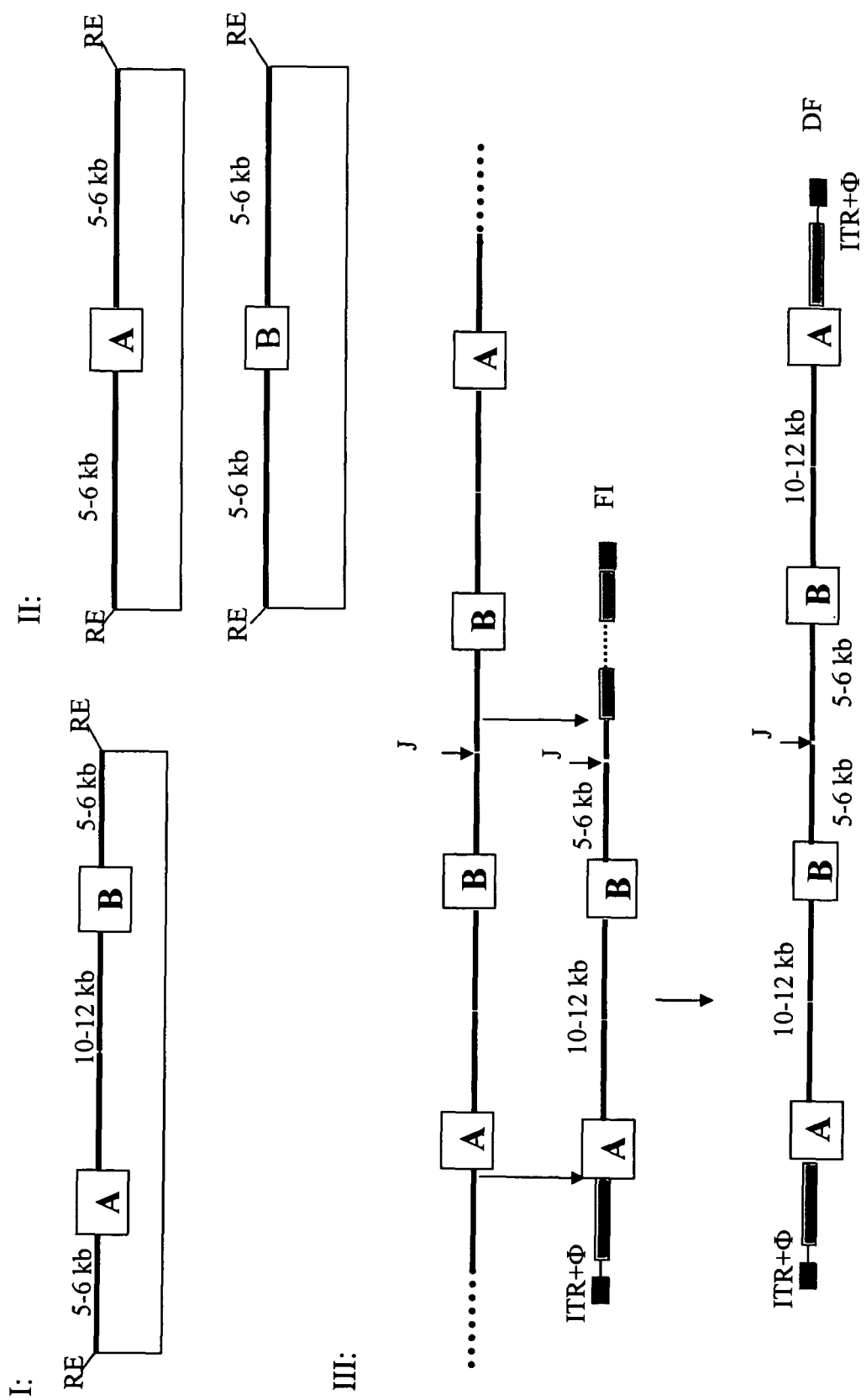
FIG. 13 is an example of the design of large molecules suitable for the transformation of primary cells. Panel I is a schematic presentation of single cosmid vector with coding regions for E1A and E1B proteins (A and B, respectively) flanked by spacer DNA. RE represents a restriction enzyme recognition site not present in the spacer DNA or E1 sequences. Panel II is a schematic representation of two separate nucleic acids (e.g., plasmids or cosmid vector) having either E1A (A) or E1B (B) coding regions flanked by spacer DNA. Panel III illustrates a situation that may occur after transformation and integration into host cell genome of a primary cell with the molecule from Panel I or with the two molecules of Panel II. In the host genome, the insert consists of an E1A region and an E1B region that are separated by spacer DNA and a second copy of that fragment (those fragments) in inverted orientation. J represents the junction between inverted repeat. If a part of these sequences (indicated by arrows) recombine in the recombinant adenovirus, the genome becomes too large to be packaged. ITR is the inverted terminal repeat, Φ represents the packaging signal, and F1 is the fragment inserted into recombinant virus, here including inverted repeat sequences. Although the presence of an inverted repeat may help in the subsequently necessary step of deleting other sequences from the virus genome, the presence of an inverted repeat sequence results in a mirror-imaged duplication of the left end of the recombined virus during replication of the virus genome and generates a genome (duplicated fragment, DF) that again is too large to be packaged due to the spacer DNA.

In a third embodiment, the sequences encoding E1A and at least one of the E1B coding sequences are unlinked by placing them on a single nucleic acid molecule, wherein E1A and at least one of the E1B coding sequences (obviously, this may as well be both E1B coding sequences) are separated by at least 4 kb, preferably at least 6 kb, more preferably at least 8 kb, still more preferably at least 10 kb, even still more preferably at least 15 kb, and most preferably at least 34.5 kb of nucleic acid, herein referred to as "spacer" or "stuffer" nucleic acid. The spacer nucleic acid sequence may advantageously have the characteristics as described infra for spacer nucleic acid sequences, in particular, the sequence lacks E1A and E1B coding sequences, may be built up at least in part of intron sequences, and may comprise regulatory sequences of the E1A and/or E1B coding sequence. It will be immediately clear to the skilled person that in an equivalent variant of the third embodiment, E1A and at least one of the E1B coding sequences may be present on different nucleic acid molecules instead of on one molecule (see, e.g., FIG. 13 I, II, and, for instance, Example 3), as long as the sequences are still separated by at least the indicated distance when different nucleic acid molecules would form a single molecule, e.g., by (homologous) recombination or ligation or end-to-end joining. The idea is that also in such a case, the E1A and at least one E1B coding sequence will still be separated by at least 4 kb, preferably at least 6 kb, more preferably at least 8 kb, still more preferably at least 10 kb, even still more preferably at least 15 kb, and most preferably at least 34.5 kb, when integrating into the genome of the precursor cell (see, e.g., Example 3 and FIG. 21). In other words, the third embodiment of the invention can, therefore, be performed by introducing into a precursor cell a single nucleic acid molecule ("molecule A") comprising the E1A and E1B-19K and E1B-55K coding sequences, at least two of these three coding sequences being separated by at least 4 kb (embodiment 3a), or equally well by introducing two or more nucleic acid molecules that when these would form a single nucleic acid molecule, would form "molecule A" (embodiment 3b). In certain aspects of the third embodiment, there are no substantially overlapping sequences between the spacer nucleic acids flanking E1A and E1B, nor in the regulatory sequences for the E1A and E1B coding sequences, in order to reduce the chance Recombinant Molecules Encoding E1A and E1B In one aspect, the invention provides a recombinant molecule comprising nucleic acid sequences encoding the adenoviral E1A proteins and at least one adenoviral E1B protein, characterized in that the nucleic acid sequence encoding E1A proteins and the nucleic acid sequence encoding at least one E1B protein are separated by at least 4 kb, preferably at least 10 kb, more preferably at least 34.5 kb. Such a molecule may be used in the method according to the invention to generate the cells according to the invention. Such a molecule may take various forms known to the person skilled in the art, such as a plasmid, cosmid, bacterial artificial chromosome, YAC, and the like.

In an equivalent embodiment, it is also possible to have the E1A and E1B protein-encoding nucleic acid initially present as separate molecules. Such molecules may optionally be capable of forming a single molecule by homologous recombination, ligation, site-specific recombination, end-to-end joining, and the like. It is, therefore, an aspect of the invention to provide a set of at least two nucleic acid molecules comprising: a) a nucleic acid molecule encoding the E1A proteins of an adenovirus, wherein the nucleic acid molecule has at least 5 kb, preferably at least 17 kb of spacer nucleic acid sequence on both sides of the E1A coding sequence, the spacer nucleic acid not encoding an E1B protein; and b) a nucleic acid molecule encoding an E1B protein of an adenovirus, wherein the nucleic acid molecule has at least 5 kb, preferably at least 17 kb of spacer nucleic acid sequence on both sides of the E1B coding sequence, the spacer nucleic acid not encoding an E1A protein. The spacer nucleic acid may be any other nucleic acid and preferably is chosen such that it is inert, i.e., does not contain coding sequences, preferably no known regulatory elements, no highly repeated regions that may lead to chromosomal instability, and the like. Preferably, the spacer nucleic acid sequence flanking E1A encoding sequences does not contain substantial homology with the spacer nucleic acid sequence flanking an E1B protein encoding sequence. The spacer fragment may include regulatory sequences of the E1A or E1B expression cassettes, such as a heterologous promoter and/or polyadenylation site.

The propagation of the recombinant molecules in a host can usually conveniently be performed when the molecules are in circular form. In certain aspects, the recombinant molecules of the invention are in a linear form. This may aid in the transfection of the precursor cell lines, which is generally more efficient when linear molecules are used. Linearization may, for instance, be effected by digestion of the recombinant molecule with one or more convenient restriction enzymes, as known to the person skilled in the art.

Cell Lines Lacking E1 Sequences in Inverted Repeat Orientation

Whatever the mechanism of generating HDEP in the absence of substantial overlap between packaging cell and recombinant adenovirus, it is likely that the first step in this process is an integration event of E1 sequences from the genome of the packaging cell into the virus genome. To accommodate for these extra sequences, the virus must subsequently delete adenovirus sequences (Murakami et al., 2002). This step may be more efficient when inverted repeats are present (Steinwaerder et al., 1999). The PER.C6® cell line contains in its genome several repeats of the pIG.E1A.E1B plasmid that was used for the generation of the cell line, some of which repeats are in inverted orientation with respect to each other. Hence, the presence of inverted repeats of the E1 region in the genome of PER.C6® cells may influence the frequency of generating HDEP. It should be noted that the formation of HDEP particles could also occur in other adenovirus packaging cell lines, but in such cell lines goes undetected due to the appearance of classical RCA. The absence of E1 sequences in inverted repeat orientation in packaging cell lines will likely result in a lower frequency or even complete absence of generation of HDEP when recombinant adenovirus is propagated on such packaging cells.

When new cell lines comprising E1 regions in their genome are generated or chosen, it may, therefore, be desirable to select clones that lack inverted repeats, but rather have only direct repeats, or even a single integration of E1 sequences. It is, therefore, an aspect of the invention to provide cells, as well as a method for providing or generating cells comprising adenoviral E1 sequences, characterized in that the method includes a step of selecting cells lacking inverted repeats comprising the E1 sequences. The invention provides a cell comprising adenovirus E1 sequences in its genome, wherein the E1 sequences include at least one functional copy of the E1A and E1B-19K and E1B-55K coding sequences, characterized in that the E1 sequences or part thereof are not present in the form of inverted repeats in the genome. In this embodiment, the cell is not a 293 cell or a derivative thereof. If inverted repeats are present, preferably such inverted repeats are not present within 10 kb in the cell and, for the present invention, inverted repeats with at least 10 kb of non-E1 intervening sequence are not further considered inverted repeats. The rationale is that when one copy of the E1 sequence is integrated somewhere on a chromosome and an inverted copy would be integrated on the same chromosome but at a distance large enough to prevent uptake of the whole segment of DNA comprising both repeats in an adenovirus particle, no problem is envisaged. Also when the distance is such that uptake of the fragment is possible (i.e., 10 kb), the duplication of the left end resulting from the inverted repeat sequence gives a virus genome that is too large to be packaged (exemplified in FIG. 13). The site of insertion of E1 sequences in the virus genome is important for the final total length of the HDEP. It is obvious that the chance that incorporation of an E1-containing genomic fragment results in a packagable genome increases when the insertion is more to the left end of the virus. If the site of insertion is just 3' from the minimal packaging signal, then the insert can be as large as 18.5 kb (including one copy of E1A and E1B and an inverted repeat sequence) and still remain packagable (assuming a left to right end duplication including 350 bp ITR and packaging signal). This does not mean that an insert of, e.g., 17 kb will easily generate HDEPs since the possible sites of integration of such a fragment that still results in a virus of packagable size is limited to 1.5 kb just 3' to the minimal packaging sequence. Thus, the frequency of generation of HDEP will decrease with increasing distance between the E1A and E1B coding regions and may very well still be below detection when that distance is much smaller then the mentioned 18.5 kb.

The same reasoning holds true for direct insertion of E1A and E1B in the absence of inverted repeat sequences. In that case, the total insertion in the genome of an adenovirus cannot be larger than 37.5 kb (including about 3 kb for the E1A and E1B region), but only when it inserts directly 3' from the minimal packaging signal. Therefore, when E1A and at least one of the E1B coding sequences are separated by at least 34.5 kb in the genome of the packaging cell, insertion of both of these sequences into a recombinant adenovirus is prevented. Furthermore, the whole adenovirus genome should then be deleted in a subsequent step, which process may further be much less efficient in the absence of inverted repeat sequences (Steinwaerder et al., 1999). In any case, irrespective of the presence of inverted E1 sequences in the genome, the chance of generating particles containing E1A and E1B sequences is reduced when the E1A and at least one of the E1B coding sequences are further apart in the genome. Hence, in certain embodiments, E1A and at least one of E1B coding sequences are separated by at least 4 kb, 6 kb, 8 kb, 10 kb, 12 kb in the genome of the cells according to the present invention. In these embodiments, preferably the E1 sequences are not present in the form of inverted repeats. Preferably, the sequences are separated by at least 15 kb and no inverted E1 sequences are present, which will ensure that the theoretical possibility of generating HDEP in such a cell line by introduction of E1 sequences from the genome of the cell line into an adenovirus is practically reduced to zero (see, FIG. 13). In other embodiments, E1A and at least one of the E1B coding sequences are separated by at least 18 kb, 20 kb, 25 kb, 30 kb. Most preferably, the sequences are separated by at least 34.5 kb. This will ensure that no single integration of both E1A and E1B derived from the genome of the cell can result in the generation of HDEP. Obviously, as indicated above, in certain equivalent embodiments, E1A and at least one E1B coding sequence are present on different chromosomes of the genome of the cell.

Methods for screening generated clones for the presence of inverted repeats of the E1 sequences are known to the person skilled in the art, and may include PCR, Southern blotting, restriction enzyme analysis, Fiber-FISH, and the like. Upon generating cell clones using a plasmid containing the E1 genes, such as the pIG.E1A.E1B plasmid (U.S. Pat. No. 5,994,128), clones can be first established, and in a screening round, those clones lacking the inverted repeat are picked for further use. The cells from the picked clones can then be suitably used for the generation of recombinant adenovirus, and it is expected that the frequency of generating HDEP on these cells will be significantly lower (or even absent) than in cells that do contain the inverted repeats. It is, therefore, another aspect of the present invention to provide a cell comprising adenovirus E1A and E1B coding sequences in its genome, characterized in that the E1 sequences are not present in the form of inverted repeats in the genome. For this aspect of the present invention, sequences that are separated by at least 10 kb of non-E1 sequence are not to be considered as inverted repeats. In a specific aspect, E1A and E1B sequences are present in the genome in at least two copies per genome. In one aspect, at least two copies comprise at least two copies present on one chromosome. In another embodiment, the cells comprise in their genome only one copy of the E1A and E1B coding regions, while lacking sequences encoding adenovirus pIX. Of course, a cell comprising only one copy of the E1 sequences in its genome should be expected to have a lower frequency (or even absence) of HDEP generation.

Use of the Cells

In another aspect, the invention provides a method for generating recombinant adenovirus in the cells of the invention. This will generate recombinant adenovirus batches having a significantly reduced frequency of HDEP compared to the batches produced on the systems known in the art, preferably no HDEP at all. In particularly preferred embodiments, the vector and packaging cell used for the generation of the recombinant adenovirus lack substantial sequence overlap (i.e., preferably less than 10 nt, or more preferably, no overlap at all), and preferably have no overlap, thereby minimizing the chance of homologous recombination between vector and sequences in the packaging cell, resulting in virus batches having no E1-containing particles (HDEP, RCA).

It is to be noted that the new cells provided according to the invention may also be used for the production of recombinant proteins as described earlier (WO 00/63403) and for producing other (non-adenoviral) viruses as described earlier (WO 01/38362).

It will be clear to the person skilled in the art that the serotype or the nature of the transgene is not critical to the invention. It will, for instance, be immediately clear that the adenoviral E1 coding sequences that are used for the generation of the cells can be taken from any convenient serotype compatible with the adenovirus that is to be propagated on the cells, such as Ad5, Ad35, Ad11, Ad16, Ad49 etc., or combinations thereof, i.e., E1A from one serotype and at least one of the E1B coding sequences from another serotype (see, e.g., WO 02/40665). It will also be clear that in many other aspects, the invention may be varied without departing from the scope or the spirit thereof. The invention will now be illustrated by the following examples, which should not be construed to limit the scope thereof.

EXAMPLES

The practice of this invention will employ, unless otherwise indicated, conventional techniques of molecular biology, cell biology, and recombinant DNA, which are within the skill of the art. See, e.g., Sambrook, Fritsch and Maniatis, *Molecular Cloning: A Laboratory Manual*, $2^{nd}$ edition, 1989; *Current Protocols in Molecular Biology*, F. M. Ausubel et al., eds., 1987; the series *Methods in Enzymology* (Academic Press, Inc.); *PCR2: A Practical Approach*, M. J. MacPherson, B. D. Harns, G. R. Taylor, eds., 1995.

Example 1

Generation of Complementing Cell Lines Using Separate Nucleic Acids Encoding E1A and E1B Proteins The complete morphological transformation of primary cells by adenovirus E1 genes is the result of the combined activities of the proteins encoded by the E1A and E1B regions. The roles of the different E1 proteins in lytic infection and in transformation have been studied extensively (reviewed in Zantema and van der Eb, 1995; White, 1995, 1996). The adenovirus E1A proteins are essential for transformation of primary cells. The concomitant induction of apoptosis is counteracted by both E1B-19K and E1B-55K, although by different mechanisms. Although the E1A region encodes several proteins, the whole region is usually referred to as the "E1A coding region" and in all embodiments, the "E1A coding sequence" as used herein refers to the sequences encoding all E1A proteins.

In rodent cells, the activity of E1A together with either E1B-19K or 55K is sufficient for full transformation, although expression of both E1B proteins together is twice as efficient (Gallimore et al., 1985; Rao et al., 1992). In human cells, however, the activity of the E1B-55K protein seems to be more important, given the observation that E1B-55K is indispensable for the establishment of an immortal transformed cell line (Gallimore et al., 1986). In adenovirus infection and virus propagation, the E1A proteins function in activation of the adenovirus genes, including E1B and other early regions, probably via interaction with the TATA-binding protein (reviewed in Zantema and van der Eb, 1995). E1B-55K expression is important in the late phase of infection for shut-off of host protein synthesis and selective transport from the nucleus to the cytoplasm of viral-encoded proteins (Babiss et al., 1985; Pilder et al., 1986). Adenoviruses that are deleted for E1B-55K show decreased replication on non-complementing human cell lines (Harada and Berk, 1999). Thus, the E1A- and E1B-55K-encoded proteins are necessary for transformation of primary human cells and for efficient virus replication in human cells.

Non-homologous recombination can result in incorporation of E1 sequences from the cellular genome of the packaging cell into the recombinant adenovirus. The helper-dependent E1-containing particles that finally result from the initial recombined adenovirus are able to complement replication of the replication-deficient vector on non-complementing (human) cells but are not capable of autonomous replication. This complementation is mediated by both E1A and E1B-55K and possibly E1B-19K functions. Thus, if the chance that both E1A and E1B-55K (and preferably E1B-19K) functions end up in the adenoviral vector is eliminated or reduced, then the formation of HDEP will be eliminated or reduced.

Here, we describe examples of functional plasmids expressing either E1A, E1A and E1B-19K, E1B (E1B-19K+ E1B-55K) or E1B-55K that are used to generate adenoviral packaging cell lines with E1A and E1B-55k regions separated from each other.

Figure 14:
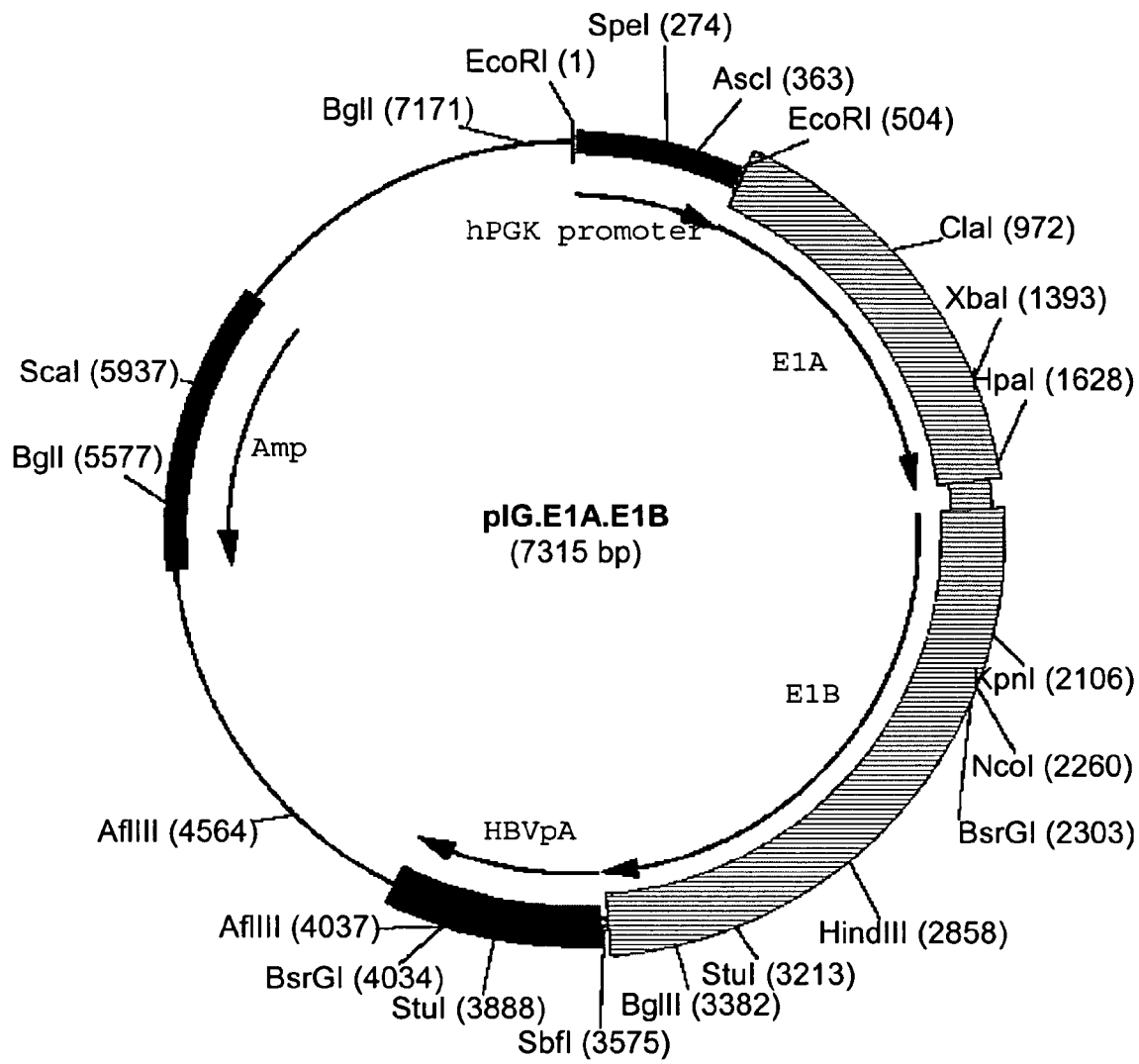
FIG. 14 is a map of pIG.E1A.E1B.

Construct pIG.E1A.E1B (FIG. 14; SEQ ID NO:1 of the accompanying SEQUENCE LISTING, incorporated herein by reference) containing the Ad5-E1 region (nucl. 459-3510 of the Ad5 genome (Genbank Acc. No. M73260) operatively linked to the human phosphoglycerate kinase (PGK) promoter and hepatitis B virus poly-adenylation sequence, has been described previously (U.S. Pat. No. 5,994,128).

Generation of Construct pIG.E1A

Construct pIG.E1A was made by digestion of pIG.E1A.E1B with HincII followed by purification of the resulting 5 kb fragment from gel using QIAEX II gel extraction kit (Qiagen) according to the manufacturer's instructions. Religation of the isolated fragment and transformation into STBL2-competent cells (Invitrogen) gave pIG.E1A (FIG. 1). This construct contains nt. 459 to 1578 from the Ad5 genome (Genbank Acc. No. M73260).

Generation of Construct pIG.E1AB21

Figure 2:
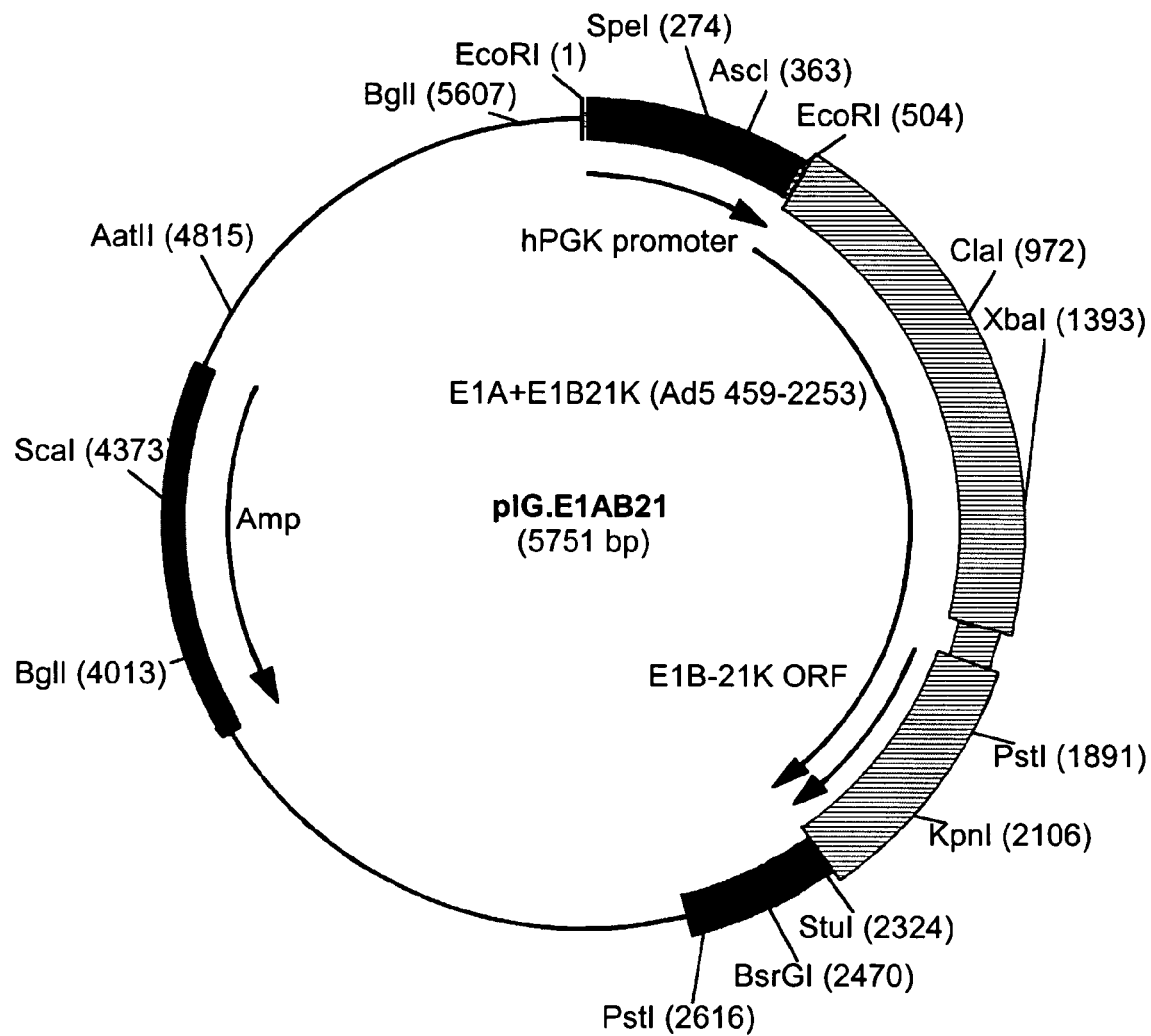
FIG. 2 depicts a map of pIG.E1AB21.

Construct pIG.E1A was digested with XbaI and HpaI and the resulting 4.8 kb fragment was isolated from gel as above. Construct pIG.E1A.E1B was digested with BsrGI and treated with Klenow enzyme (New England Biolabs) to blunt the 5' protruding ends. DNA was then purified with the QIAquick PCR purification kit (Qiagen) according to the manufacturer's instructions and subsequently digested with XbaI. The resulting 913 bp fragment containing the 3' part of E1A and the E1B19K coding sequence was isolated from gel as described. Ligation of the two isolated fragments and transformation into DH5α-T1$^r$ cells (Invitrogen) gave construct pIG.E1AB21 (FIG. 2). This construct thus contains nt. 459 to 2253 from the Ad5 genome (Genbank Acc. No. M73260), whereby the E1A sequence is driven by the PGK promoter and the E1B promoter drives the E1B-19K gene.

The Ad5 E1B-19K gene is sometimes also referred to as the Ad5 E1B-21K gene because the predicted amino acid sequence constitutes a 20.6 KD protein (for instance, several of the plasmids and primers in this application have 21K as part of their names).

Generation of Construct pCR5B

A construct containing the Ad5-E1B region was then generated as follows. First, a PCR fragment was generated with primers 5E1Bfor-1: 5'-CGG AAT TCG GCG TGT TAA ATG GGG CG-3' (SEQ ID NO:2) and 5E1B-rev: 5'-TAG CAG GCG ATT CTT GTG TC-3' (SEQ ID NO:3), using pIG.E1A.E1B DNA as template and Pwo DNA polymerase (Roche) according to the manufacturer's instructions with DMSO at 3% final concentration. The amplification program was 94° C. for two minutes followed by 30 cycles of (94° C. for 30 seconds, 50° C. for 30 seconds and 72° C. for one minute) and ended by 72° C. for ten minutes. The resulting 481 bp amplified fragment was purified with the QIAquick PCR purification kit (Qiagen) and ligated to the pCR-ScriptAmp vector from the PCR cloning kit (Stratagene) in the presence of SrfI enzyme according to the manufacturer's instructions. The (blunt) ligation gave two orientations of the insert in the vector of which the one with the largest fragment between the EcoRI site in the (5') end of the insert and the EcoRI site in the vector was arbitrarily chosen. This resulted in construct pCR5B. Correct amplification of the target sequence (between KpnI and EcoRI sites) was verified by sequencing.

Figure 3:
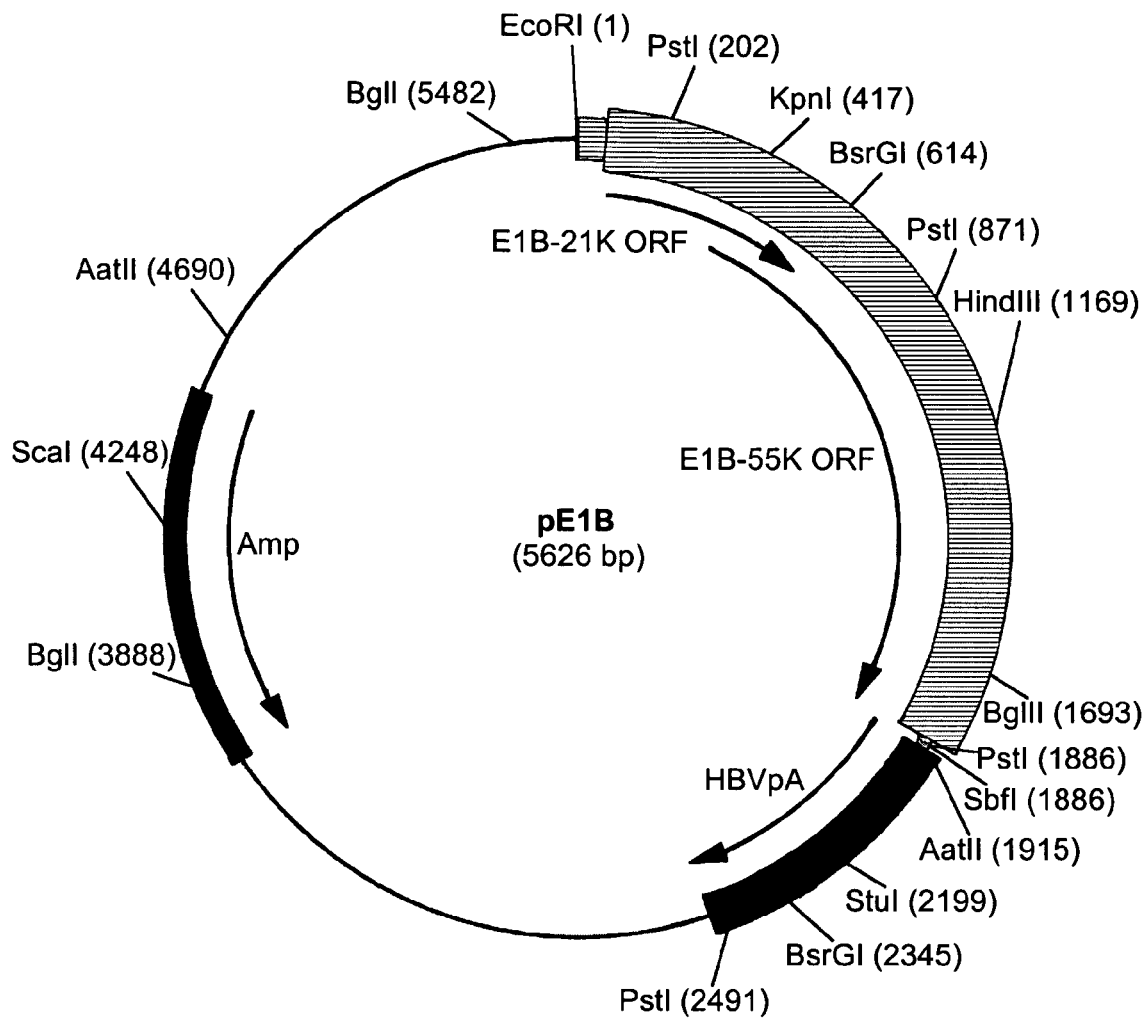
FIG. 3 is an illustration of a map of pE1B.

Generation of Construct pE1B pCR5B was digested with KpnI and EcoRI and the 415 bp fragment was isolated from gel using the QIAquick gel extraction kit (Qiagen). Construct pIG.E1A.E1B was then also digested with EcoRI and KpnI and the resulting 5.2 kb vector fragment was isolated from gel as above. Ligation of the isolated fragments and transformation into DH5α-T1$^r$ cells (Invitrogen) resulted in construct pE1B (FIG. 3). The E1B sequence in this construct constitutes nt. 1642 to 3510 from the Ad5 genome.

The transforming ability of the new constructs, in comparison with the full length Ad5E1 expression construct, was then tested. Hereto, primary human embryonic retina (HER) cells were isolated (see, e.g., Byrd et al., 1982, 1988) and seeded in 6 cm dishes in DMEM medium (Gibco BRL), supplemented with 10% heat-inactivated Fetal Bovine Serum (FBS, Gibco BRL). At 60 to 70% confluency, cells were transfected with, in total, 20 μg DNA/dish, using the CaPO$_4$ co-precipitation kit (Invitrogen) according to the manufacturer's instructions. Two weeks later, transformed clones were visible as foci in a monolayer of primary cells. Cells in a focus showed a clearly different morphology compared with the primary cells. Table I depicts the amounts of transformed clones that were obtained with each of the transfections.

The results confirm previous observations that primary cells can be transformed with Ad5-E1A and E1B19K genes (pIG.E1AB21). It should be noted that these foci were generally smaller than the ones obtained with the transfection where the complete E1B region was present. Also, after picking the foci resulting from transfections with construct pIG.E1AB21 and seeding into 96-well plates, no sustained cell growth was obtained and all cells died. In all other cases, most of the picked foci resulted in viable cell clones.

Since transfection with pIG.E1AB21 initially resulted in transformed cells, it is possible to re-transfect the cells with an E1B-55K expression construct, e.g. five to ten days following the first transfection. This ensures that cells are obtained that have incorporated both expression cassettes on different loci in the genome.

This experiment further confirms that it is possible to generate and establish transformed cell clones by using two separate plasmids for the E1A and E1B genes (pIG.E1A+pE1B). However, because both plasmids were transfected together and contain considerable sequence overlap (plasmid backbone and promoter/polyA), it is possible that integration of E1A and E1B took place in the same locus in the genome.

This may be avoided using fragments with expression cassettes only (no vector sequences) and having no sequence overlap. The sequence overlap can be removed from regulatory elements, such as the promoters and polyadenylation (polyA) sequences, by using different regulatory sequences for the two expression constructs with the E1A and E1B sequences. Preferably, these sequences are sufficiently divergent to prevent overlap that could lead to the formation of paired structures found during a homologous recombination process. Any promoter and polyA sequence can be used. Preferably, the regulatory sequences are different from those from the transgenes in the recombinant adenovirus that will be propagated on these cells. Obviously, this can only be determined when a given recombinant adenovirus is propagated on these cells at a later stage and will depend on the particular recombinant adenovirus. Hence, it is convenient to choose the regulatory sequence of such transgenes later, such that they differ from those of the E1A and E1B sequences in the cells that are established by the present invention. However, since many currently available recombinant adenovirus vectors carry transgenes regulated by a CMV promoter and an SV40 polyA sequence, the preferred regulatory sequences for the E1A and E1B constructs as exemplified herein are different from the CMV promoter and the SV40 polyA sequence. In view of regulatory issues, these regulatory sequences are preferably not of viral origin.

To this end, the plasmids described above are further modified as described below.

Generation of Construct pCC.E1A and pCC.E1AB21

The E1A sequence was amplified with the following primers: 5E1A-For: 5'-CCG AAT TCG ATC GTG TAG TG-3' (SEQ ID NO:4) and 5E1A-rev: 5'-CGG GAT CCA TTT AAC ACG CCA TGC AAG-3' (SEQ ID NO:5). The reaction was done on pIG.E1A.E1B template DNA using Pwo DNA polymerase (Roche) according to the manufacturer's instructions but with a final concentration of 3% DMSO. The PCR program was set on 94° C. for two minutes followed by 30 cycles of (94° C. for 30 seconds, 58° C. for 30 seconds and 72° C. for 120 seconds) and ended by 72° C. for eight minutes. The resulting 1.2 kb fragment contains the E1A sequence from Ad5 (nucleotide 459 to 1655 as in Genbank Acc. No. M73260) flanked by EcoRI (5') and BamHI (3') sites.

A second PCR fragment was generated using primer 5E1A-For with reverse primer: 5E1AB21-rev: 5'-CGG GAT CCT CAT TCC CGA GGG TCC AG-3' (SEQ ID NO:6), using the same conditions.

The resulting 1.8 kb fragment contains the E1A and E1B-19K sequence from Ad5 (nucleotide 459 to 2244 as in Genbank Acc. No. M73260) flanked by EcoRI (5') and BamHI (3') sites. Both PCR fragments were isolated from agarose gel, purified with QIAEX II gel extraction kit (Qiagen) and cloned in a PCR cloning vector; pCR-TOPOblunt (Invitrogen) and the sequence was verified. The constructs were then digested with EcoRI and BamHI and the insert fragments were isolated from gel using the QIAEX II gel extraction kit (Qiagen) as above.

Figure 4:
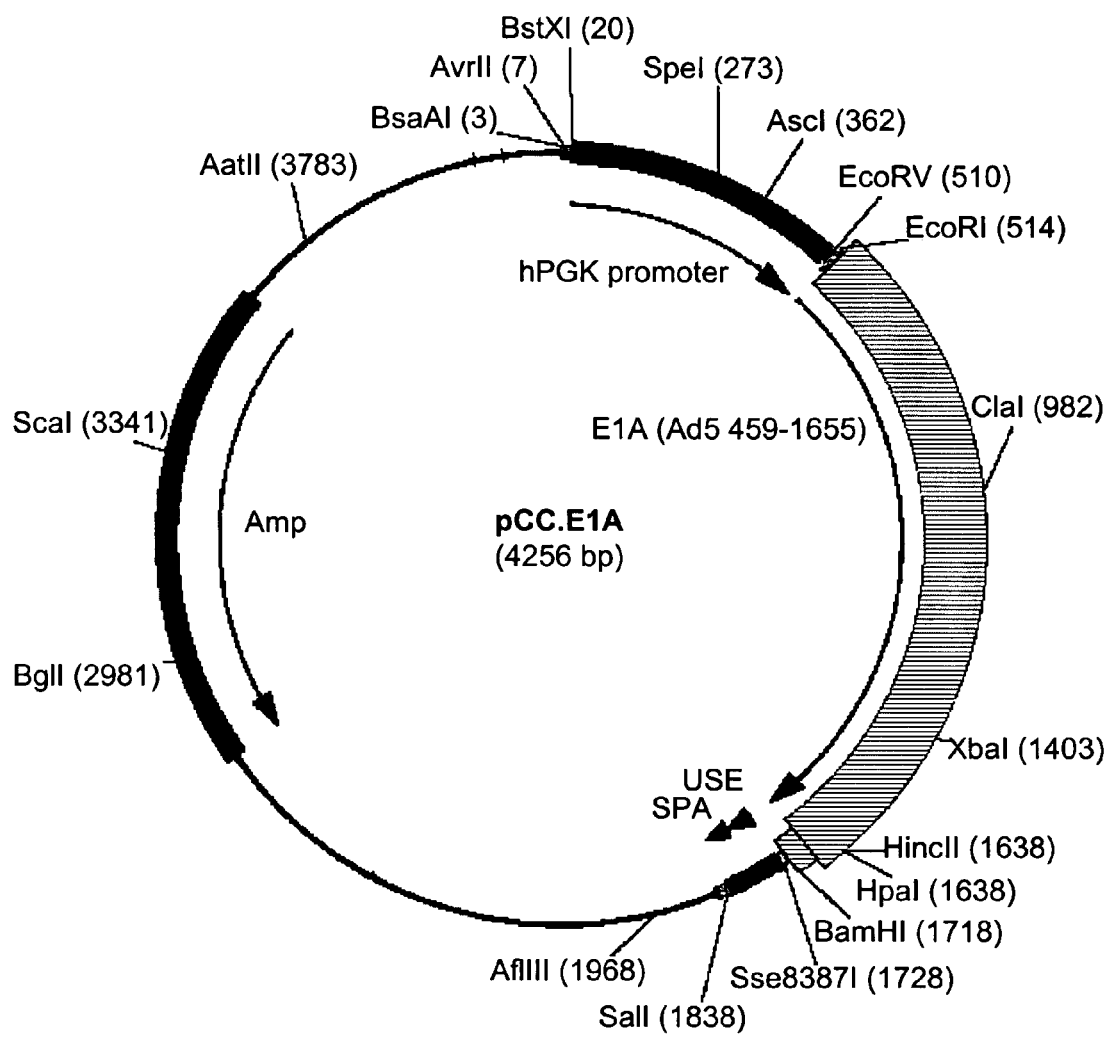
FIG. 4 depicts a map of pCC.E1A.
Figure 5:
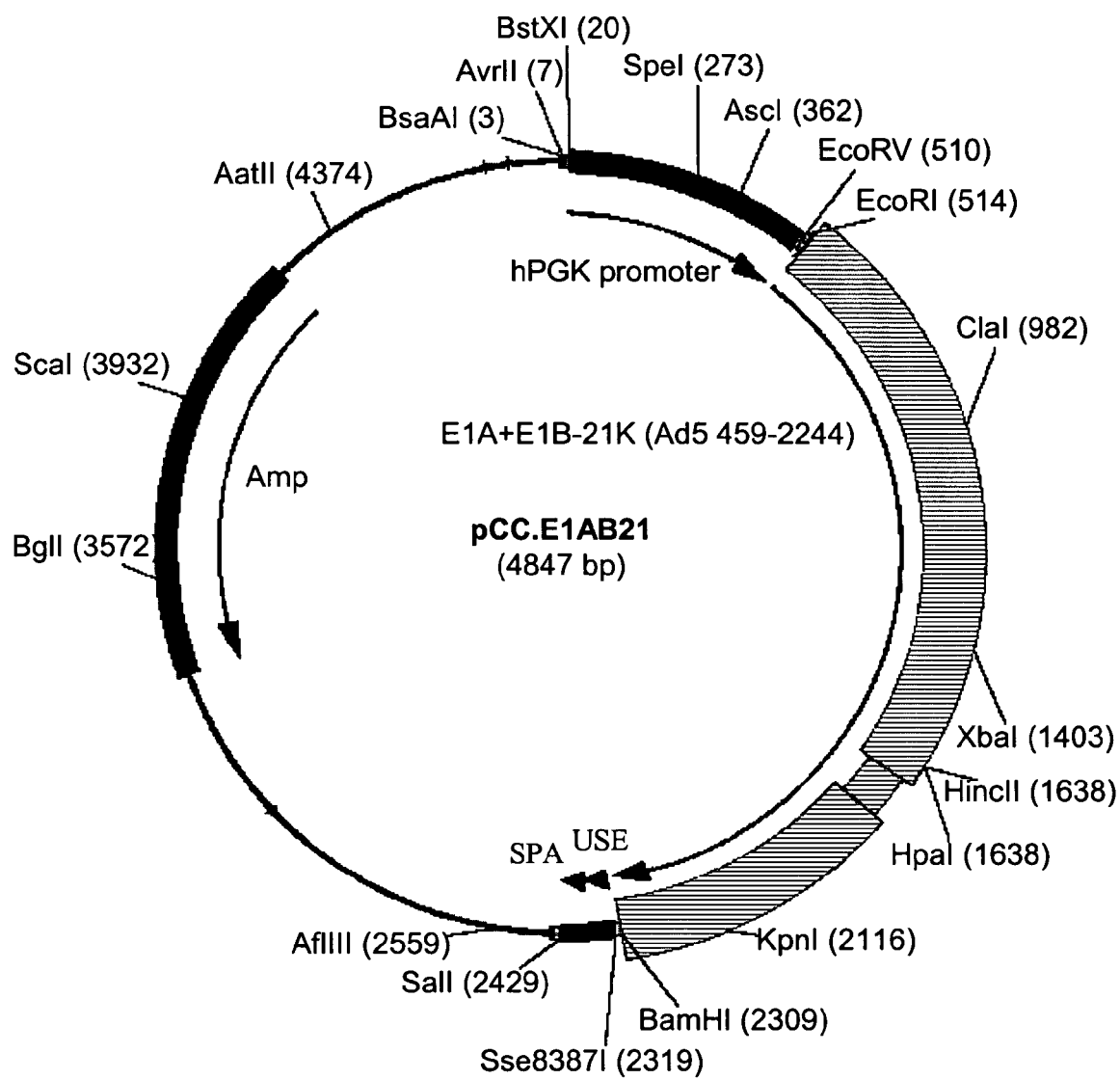
FIG. 5 is a map of pCC.E1AB21.

Each of the isolated fragments was then ligated into vector pCC101 (see below) that was first digested with EcoRI and BamHI and purified from gel as above. Transformation into electro-competent DH10B cells (Invitrogen) generated constructs pCC.E1A (FIG. 4) and pCC.E1AB21 (FIG. 5). A synthetic polyadenylation signal (SPA) is present in these plasmids (derived from construct pCC271 as described in WO 02/40665).

Figure 6:
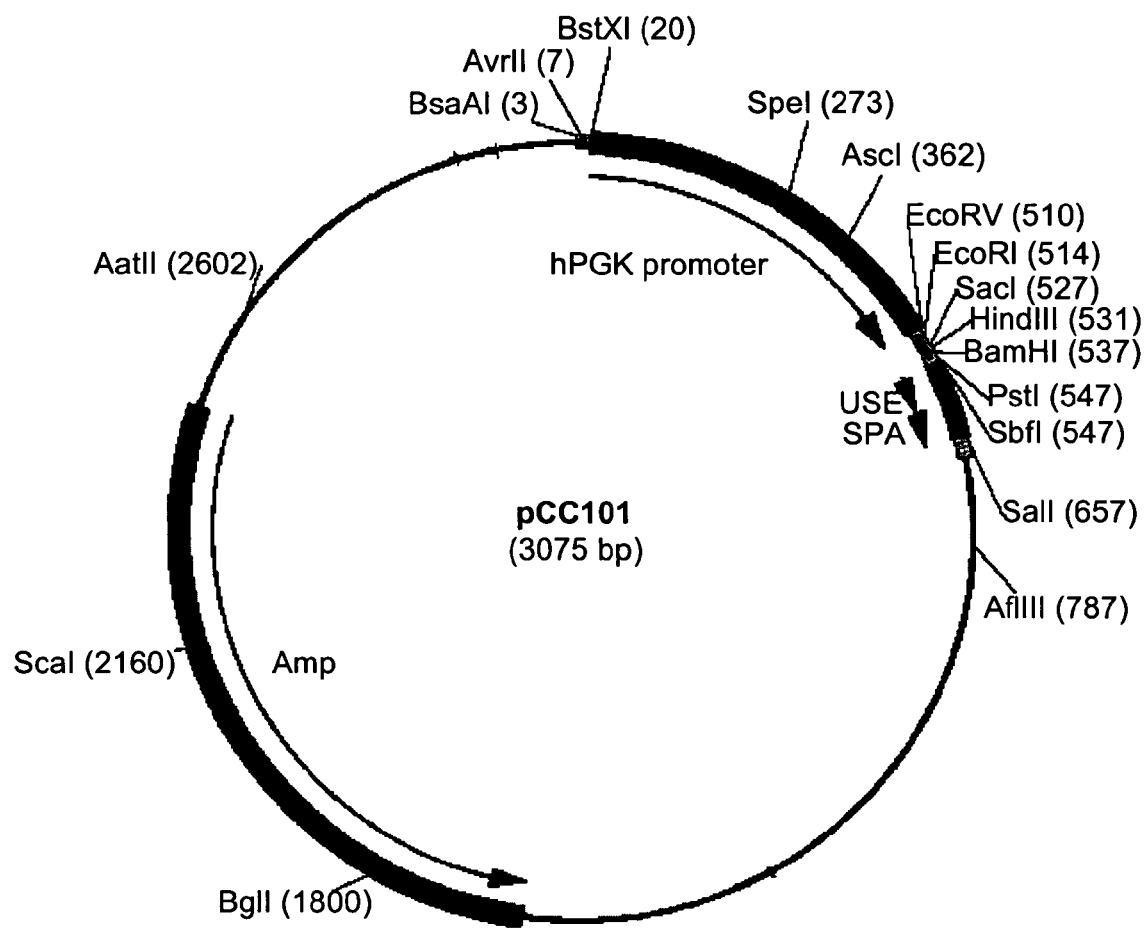
FIG. 6 is an illustration of a map of pCC101.

Generation of pCC101 pCC100 (see below) was digested with XbaI and the resulting linear fragment was purified from gel using the QIAEX II gel extraction kit as above. A linker was prepared by annealing the oligonucleotides X-SM-1: 5'-CTAGGTCGAC-CAATTG-3' (SEQ ID NO:7) with X-SM-2: 5'-CTAGCAAT-TGGTCGAC-3' (SEQ ID NO:8). Hereto, 1 μg of each oligonucleotide was mixed with 2 μl 10×NEB2 buffer (NEB) and milliQ H$_2$O to a final volume of 20 μl. The mixture was placed at 98° C. and slowly cooled to 4° C. in a PCR machine (cooling rate of 2° C./minute). The annealed linker was then ligated to the isolated XbaI-digested fragment using a 4× molar excess of linker over fragment. The ligated DNA was purified with the QIAquick PCR purification kit (Qiagen) according to the manufacturer's instructions and digested with XbaI to remove self-ligated vector DNA. Following heat-inactivation of the XbaI enzyme, the mixture was then used to transform DH5α-T1$^r$-competent cells resulting in pCC101 (FIG. 6).

Generation of pCC100

Construct pCC271 (described in WO 02/40665) was digested with EcoRI and PstI and the 3 kb vector fragment was isolated from gel as described above. A linker was prepared by annealing oligonucleotide EcoPst-3: 5'-AAT TGA TAT CGA ATT CGC CGA GCT CGT AAG CTT GGA TCC CTG CA-3' (SEQ ID NO:9) with oligonucleotide EcoPst-4: 5'-GGG ATC CAA GCT TAC GAG CTC GGC GAA TTC GAT ATC-3' (SEQ ID NO:10). Hereto, oligonucleotides were mixed as described above and annealed by incubation at 98° C. for two minutes, 65° C. for 30 minutes and room temperature for two hours. The isolated vector fragment was then ligated to excess annealed oligo and transformed into DH5α-T1$^r$-competent cells resulting in construct pCC 100.

Generation of pCC200

Figure 15:
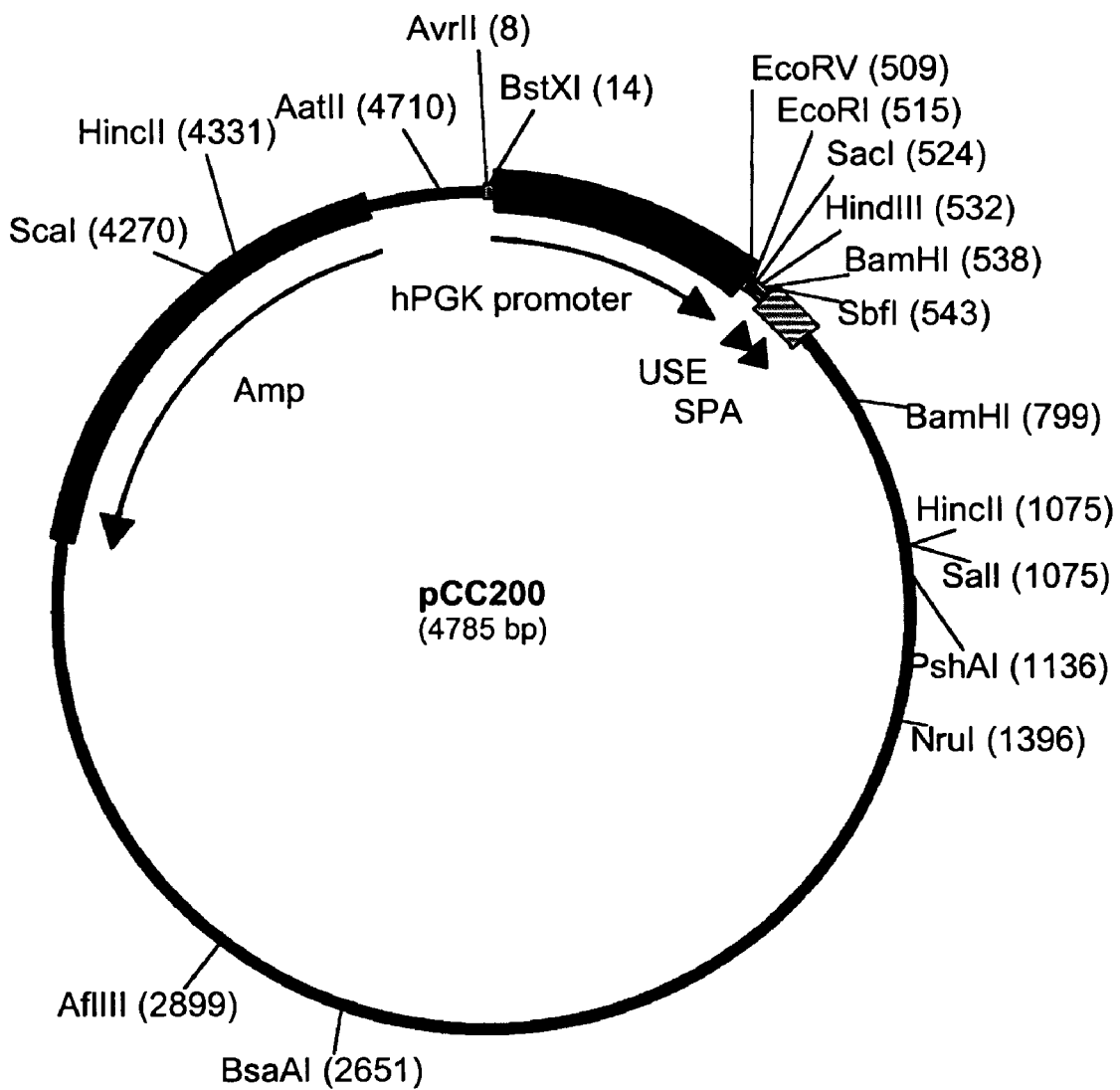
FIG. 15 depicts a map of pCC200.

Plasmid pBR322 (GenBank J01749.1) was digested with EcoRI and then blunted with Klenow enzyme, followed by purification with QIAquick PCR purification kit (Qiagen). After a second digestion with NheI, the 4150 bp vector fragment was isolated from agarose gel using the QIAEX II gel extraction kit (Qiagen). In parallel, construct pCC100 was digested with BsaAI, blunted with Klenow enzyme and purified with the QIAquick PCR purification kit (Qiagen), followed by a second digestion with XbaI and isolation of the 350 bp fragment from agarose gel. The fragments were then ligated and transformed into chemical-competent STBL-2 cells (Invitrogen), resulting in pCC200 (FIG. 15).

Generation of pCC105

Construct pCC105 contains the human PGK promoter and a poly-adenylation sequence derived from the human COL1A2 gene. First, the COL1A2 poly-adenylation sequence (Natalizio et al., 2002) was amplified by PCR from human genomic DNA as described by the authors using recombinant Taq polymerase (Invitrogen) and primers COL1A2F: 5'-CAG CTA GCC TGC AGG AAG TAT GCA GAT TAT TTG-3' (SEQ ID NO: 11) and COL1A2R-sal: 5'-ACA CGT CGA CGG CTG GTA GAG ATG C-3' (SEQ ID NO:12).

Figure 7:
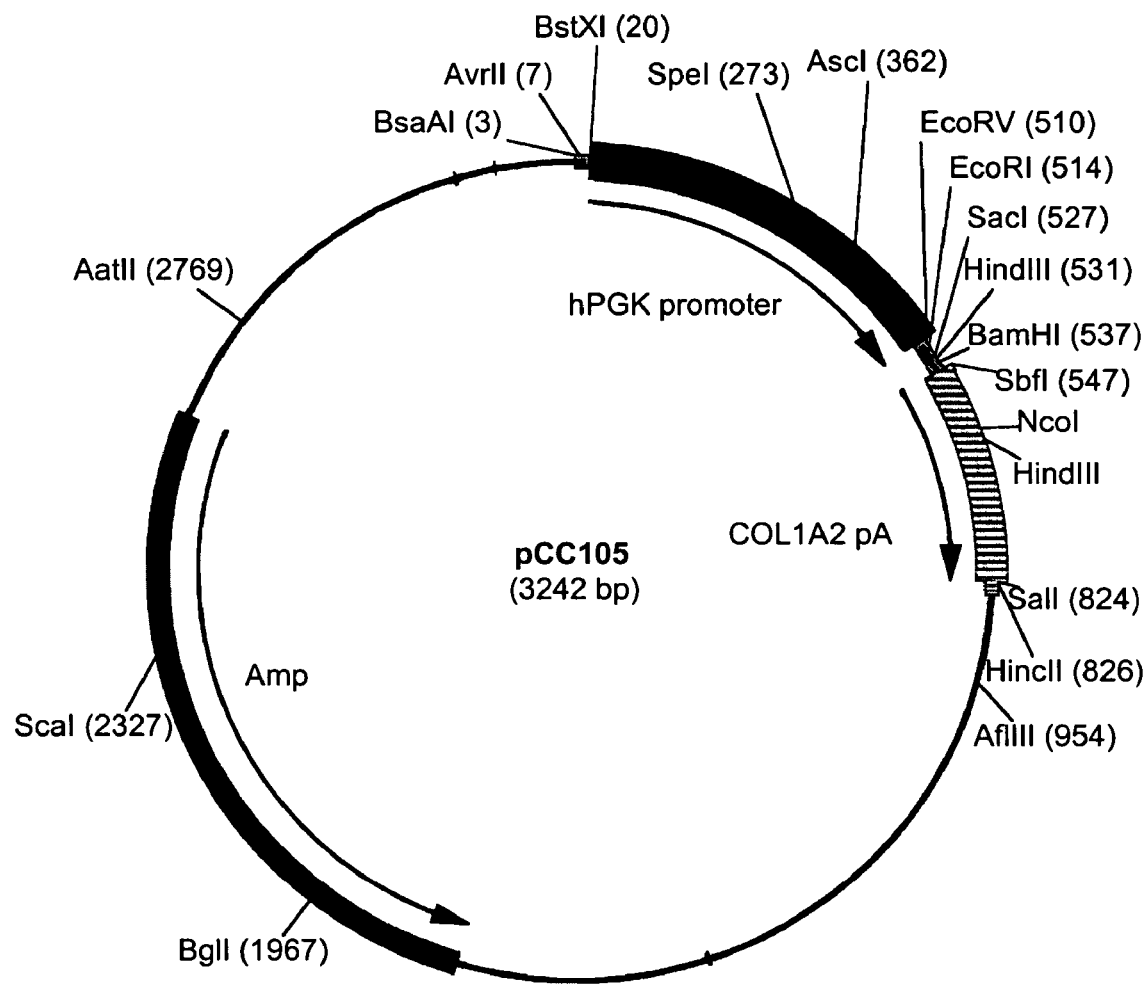
FIG. 7 depicts a map of pCC105.

Herewith, the published sequence is extended at the 5'-end by an SbfI restriction sequence and at the 3'-end by an SalI restriction sequence. The resulting PCR fragment was cloned into pCR-TOPO-TA using the pCR-TOPO4 TA cloning kit (Invitrogen). After verification of the insert by sequencing, the 277 bp insert was isolated from the TOPO vector by digestion with SbfI and SalI, and purified with the QIAquick PCR purification kit (Qiagen). In parallel, the plasmid pCC101 was also digested with SbfI and SalI, followed by gel electrophoresis. The 2965 bp vector fragment was isolated from agarose gel using a GeneClean Kit (Bio101) according to the manufacturer's instructions. This vector fragment was ligated to the purified COL1A2pA fragment in equimolar amounts and transformed to chemical-competent STBL-2 cells (Invitrogen). This gave plasmid pCC105 (FIG. 7).

Generation of pCC205

Figure 16:
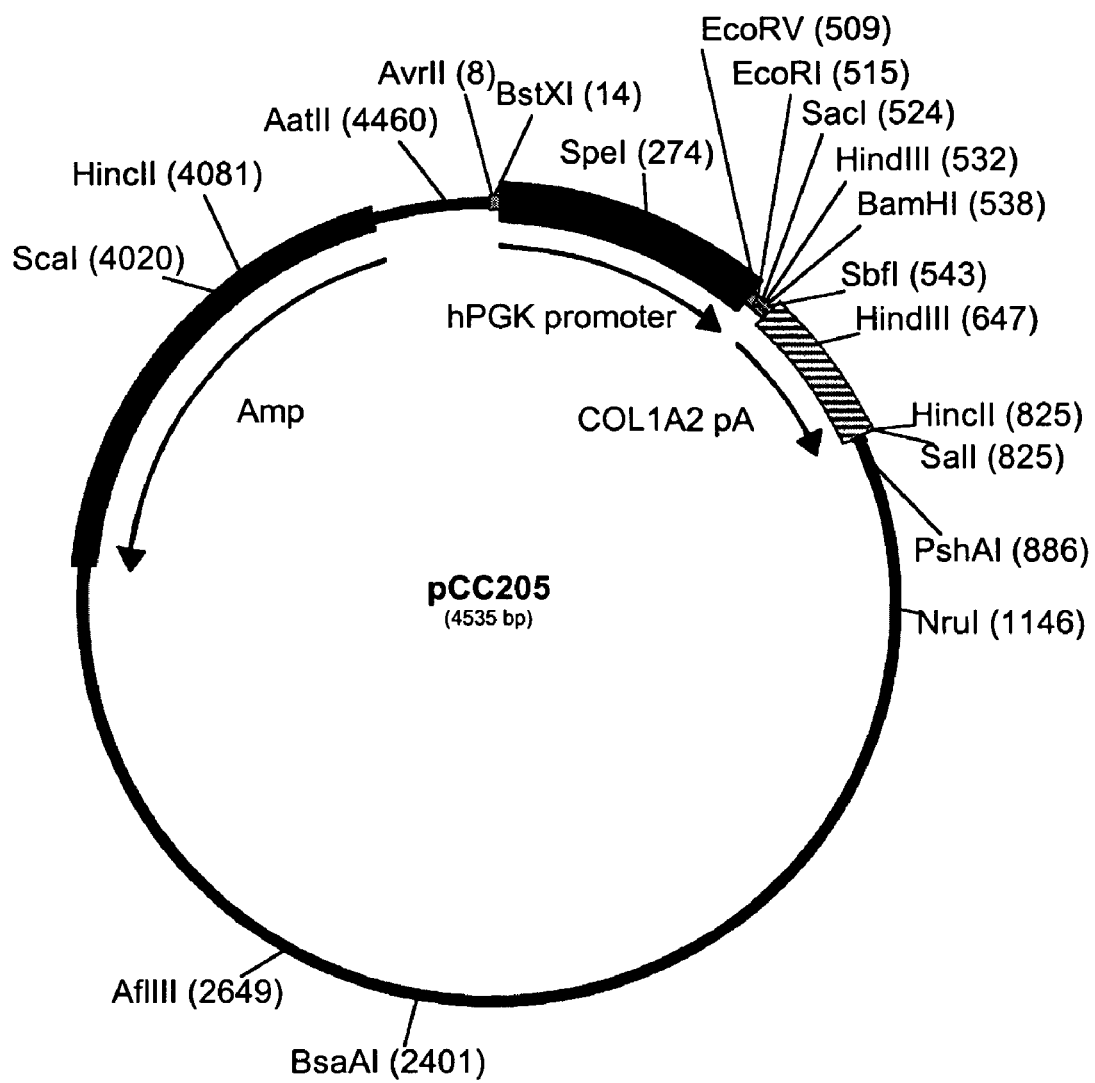
FIG. 16 is an illustration of a map of pCC205.

Construct pCC205 was made by digestion of pCC200 with SalI and EcoRI, followed by purification of the 4225 nt vector fragment from agarose gel, using QIAEX II gel extraction kit (Qiagen). In parallel, the 310 nt COL1A2 polyA was isolated from construct pCC105 by digestion with EcoRI and SalI, followed by gel electrophoresis and purification of the fragment using the QIAEX II gel extraction kit. The two fragments were then ligated in equimolar amounts and transformed to DH5α-T1r, resulting in pCC205 (FIG. 16).

Cloning of pCC.55Kcol

Figure 8:
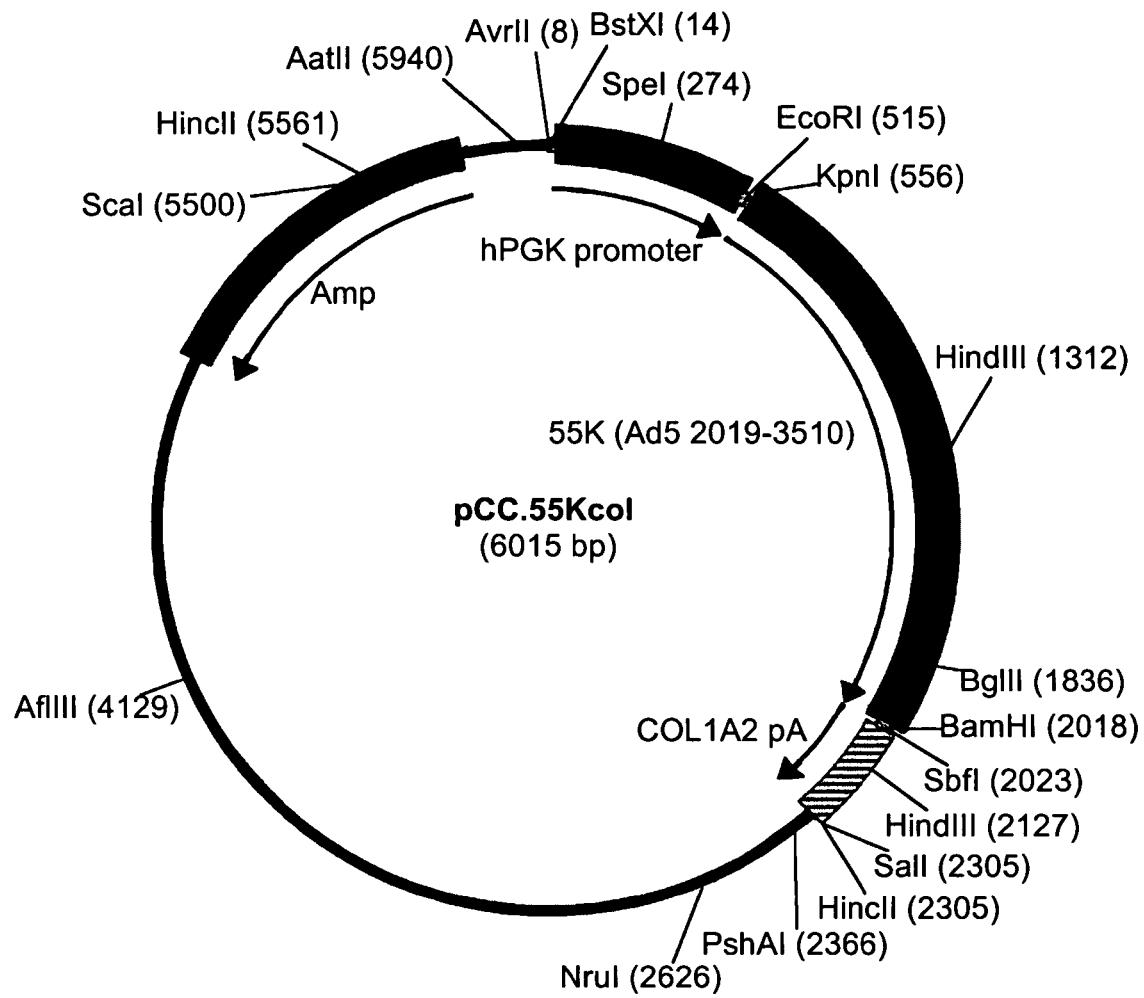
FIG. 8 is a map of pCC.55Kcol.

Vector pCC205 is used for the construction of a plasmid expressing the Ad5 E1B-55k protein. Hereto, a PCR product is generated using the following primers: 55KforE: 5'-GGA ATT CGC CAC CAT GGA GCG AAG AAA CCC ATC TGA-3' (SEQ ID NO:13) and 55KrevB: 5'-gga tcc TCA ATC TGT ATC TTC ATC GCT AGA GCC-3' (SEQ ID NO:14). PCR is performed with Pwo DNA polymerase according to the manufacturer's protocol in the presence of 3% DMSO. The amplification is done on pIG.E1A.E1B and the program is set at 94° C. for two minutes followed by 30 cycles of (94° C. for 30 seconds, 60° C. for 30 seconds and 72° C. for 90 seconds) and ended by 72° C. for eight minutes. The resulting 1510 bp amplified fragment contains the E1B-55K sequence nt. 2019 to 3510 from the Ad5 sequence. The fragment is purified with the QIAquick PCR purification kit (Qiagen), digested with EcoRI and BamHI followed by gel electrophoresis for the removal of the cleaved ends. This fragment is then purified from agarose gel using the GeneCleanII kit (Bio101) and ligated to pCC205, which is also digested with EcoRI and BamHI and isolated from agarose gel as described above. The ligation mixture is transformed to chemical-competent STBL2 cells (Invitrogen) resulting in construct pCC.55Kcol (FIG. 8).

Cloning of pIG.E1B

A PCR fragment was generated with Pwo DNA polymerase (Roche) according to the manufacturer's instructions in the presence of 3% DMSO. The following primers were used in the amplification reaction: 5E1Bstart: 5'-GGA ATT CCT CAT GGA GGC TTG GG-3' (SEQ ID NO:15) and 5E1Brev2: 5'-GTG TCT CAC AAC CGC TCT C-3' (SEQ ID NO:16). The amplification was done on pIG.E1A.E1B and the program was set on 94° C. for two minutes followed by five cycles of (94° C. for 30 seconds, 56° C. for 30 seconds and 72° C. for 60 seconds) these cycles were then followed by another 35 cycles (94° C. for 30 seconds, 60° C. for 30 seconds and 72° C. for 60 seconds) and ended by 68° C. for eight minutes. The 390 nt PCR fragment was then digested with KpnI and EcoRI resulting in a 347 nt fragment that was isolated from agarose gel using the QIAEX II Gel Extraction Kit (Qiagen).

Figure 9:
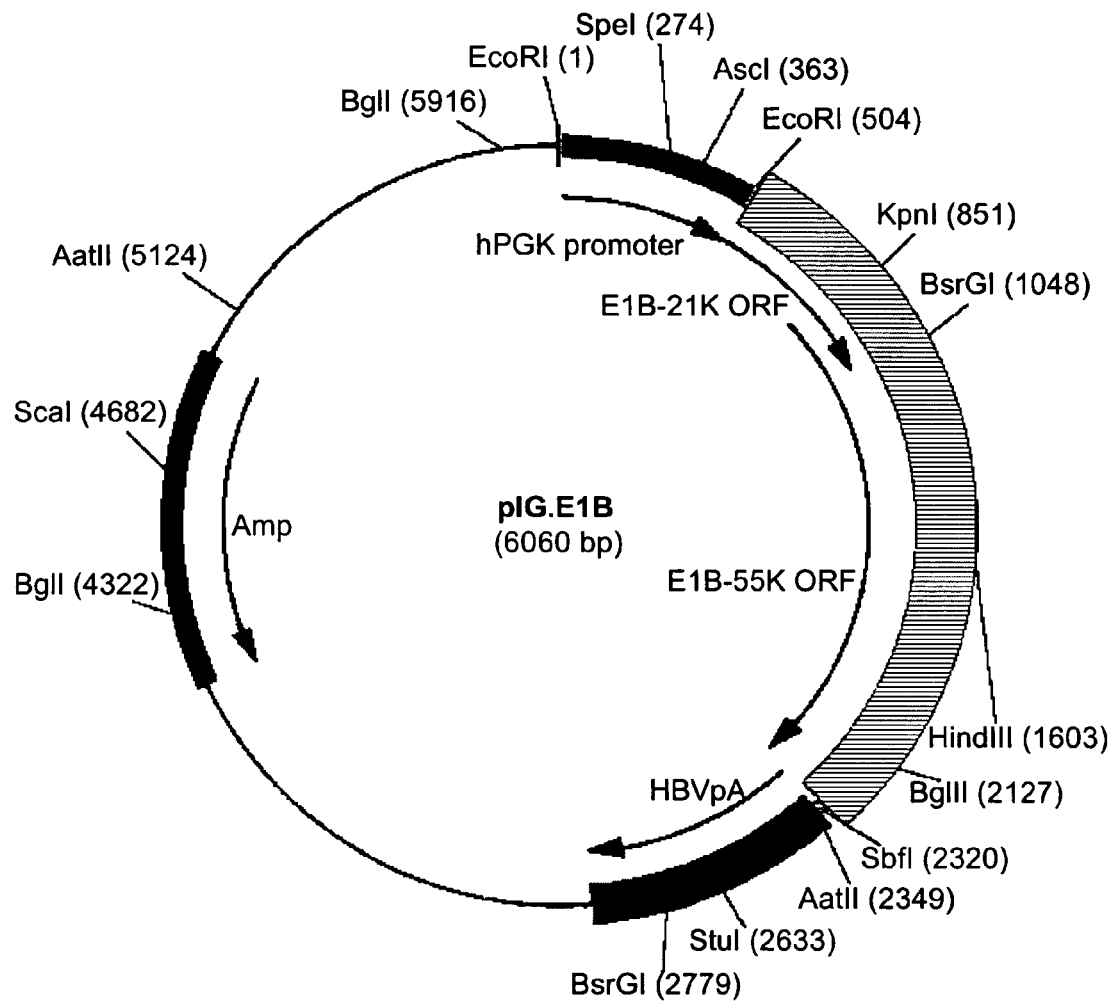
FIG. 9 depicts a map of pIG.E1B.

This fragment was then ligated to the 5713 bp pIG.E1A.E1B vector fragment resulting from digestion with KpnI and partially with EcoRI, subsequent isolation from gel and purified with the QIAEX II gel extraction kit (Qiagen). After ligation, the mixture was transformed into chemically competent STBL-2 cells, resulting in the plasmid pIG.E1B (FIG. 9). pIG.E1B contains nt. 2019 to 3510 from the Ad5 genome.

Cloning of pCC.E1Bcol

Figure 10:
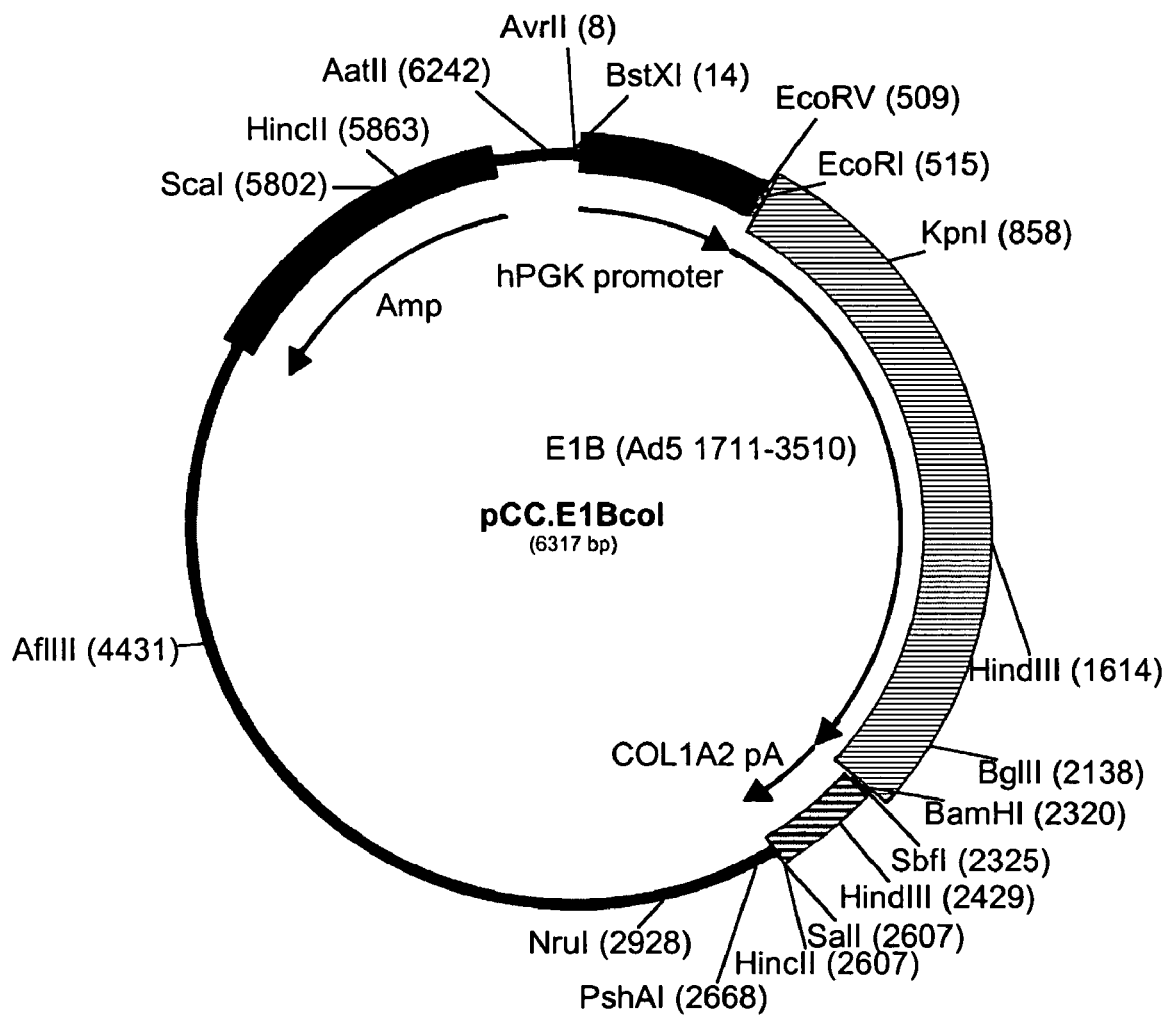
FIG. 10 is an illustration of a map of pCC.E1Bcol.

For the construction of a plasmid carrying both the 19K and 55K Ad5 E1B coding sequences, the plasmid pCC.55Kcol is digested with EcoRI and KpnI. The 5970 nt vector fragment is isolated by gel electrophoresis and purified from agarose gel with the GeneCleanII kit (Bio101) as above. Construct pIG.E1B is then also digested with KpnI and EcoRI and the 347 nt fragment is isolated from gel and purified with the QIAquick gel extraction kit (Qiagen). Ligation of this insert and the isolated pCC.55Kcol vector fragment and transformation into STBL2 cells gives construct pCC.E1Bcol (FIG. 10). This construct contains nt. 1711 to 3510 from the Ad5 genome sequence.

Cloning of pEC.E1B

Figure 11:
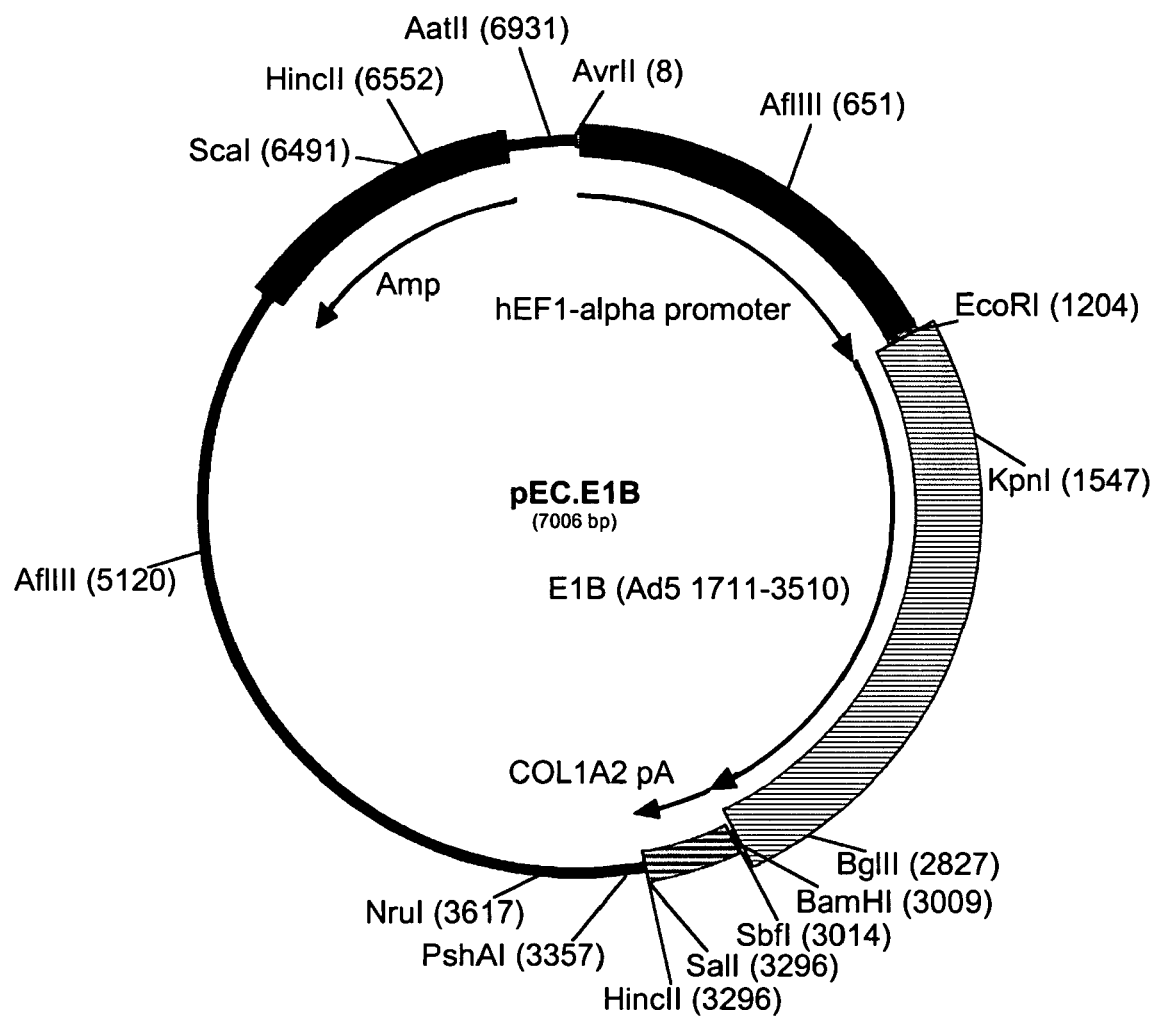
FIG. 11 is a map of pEC.E1B.

The Human Elongation Factor 1-α promoter (EF1-α) is isolated from plasmid pEF/myc/nuc (Invitrogen) by digestion with EcoRI and PmlI. After digestion, the fragment is blunted with Klenow enzyme and the 1183 nt EF1-α promoter fragment is then isolated by gel electrophoresis and purified with the GeneCleanII kit (Bio101). In parallel, the vector pCC.E1Bcol is digested with BstXI, followed by T4 DNA polymerase treatment to make the ends blunt and purified over a PCR purification column (Qiagen). Then, a second digestion is performed with EcoRV, followed by gel electrophoresis. The 5827 nt vector fragment is then purified with the GeneCleanII kit (Bio101). Both the EF1-α fragment and vector fragment are ligated together in an equimolar amount and transformed to chemical-competent STBL-2 cells (Invitrogen), which results in the plasmid pEC.E1B (FIG. 11) that contains the same Ad5-E1B sequence as in plasmid pCC.E1Bcol.

Cloning of pSC.55K

Figure 12:
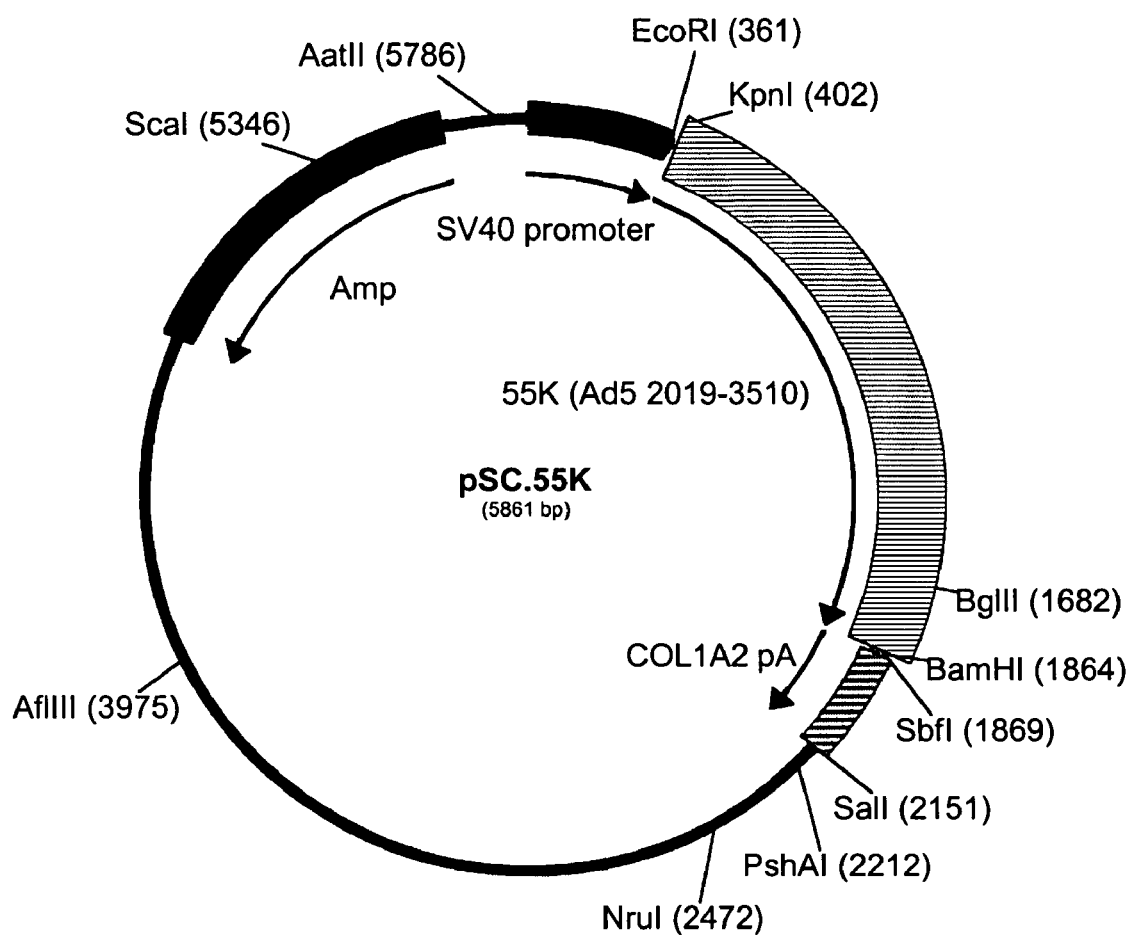
FIG. 12 depicts a map of pSC.55K.

The SV40 promoter was amplified from pEF/myc/nuc plasmid DNA (Invitrogen) by using recombinant Taq DNA polymerase (Invitrogen) and the following primers: SV40.forS: 5'-CAA CTA GTA CAT GTG GAA TGT GTG TCA GTT AGG-3' (SEQ ID NO:17) and SV40.RevERI: 5'-GGA ATT CAG CTT TTT GCA AAA GCC TAG G-3' (SEQ ID NO:18). The amplification program was set at 94° C. for two minutes followed by five cycles of (94° C. for 30 seconds, 48° C. for 30 seconds and 72° C. for 45 seconds) then 25 additional cycles of (94° C. for 30 seconds, 58° C. for 30 seconds and 72° C. for 45 seconds) and ended by 68° C. for eight minutes. The resulting 357 bp amplified fragment (nucleotide 266 to −71 from SV40 sequence GenBank Acc. No. J02400) was isolated from agarose gel with the QIAEX II gel extraction kit (Qiagen). This fragment was then cloned into pCR-TOPO, using the PCR TOPO4 blunt cloning kit (Invitrogen). After sequence verification, the 357 bp insert was isolated from the TOPO vector by digestion with EcoRI and SpeI, and isolated from agarose gel with the QIAEX II gel extraction kit (Qiagen). In parallel, the plasmid pCC.55Kcol (which has a pBR322-backbone) is digested with AvrII and EcoRI, followed by gel electrophoresis. The 5508 nt vector fragment is isolated from gel as described above and ligated in equimolar amount to the digested PCR fragment. The ligation mixture is transformed into chemical-competent STBL-2 cells, resulting in the plasmid pSC.55K (FIG. 12) that contains the same Ad5 E1B-55K sequence as in pCC.55Kcol.

To generate transformed clones from primary HER cells, DNA fragments containing the appropriate expression cassettes are isolated from gel. The elimination of (overlapping) vector sequences is believed to reduce the chance of co-integration. Hereto, pCC.E1A and pCC.E1AB21 are digested with BsaAI and AflIII and the insert fragments are purified from gel using an ELU-Trap apparatus (Schleier and Schuell) according to the manufacturer's instructions. This apparatus enables isolation of large amounts of DNA fragments. Constructs pEC.E1B and pSC.55K are digested with AatII/HincII and AflIII/HincII, respectively, and insert fragments are isolated as above. Primary HER cells are cultured and transfected as described above. Fragments isolated from pCC.E1A and pEC.E1B are combined for transfection. The DNA fragments isolated from pCC.E1AB21 are combined with pSC.55K or transfected alone. The latter cultures are then retransfected with the DNA fragment isolated from pSC.55K seven to ten days following the first transfection, depending on the size of the observed clones. One day before transfection, half of the dishes transfected with E1AB21 alone is passed to 10 cm dishes and then re-transfected, the other half of the dishes is re-transfected without prior passage.

The transformed clones that result from these transfections are picked and further expanded in 96-well plates and subsequent larger formats. The integration site and copy number of the fragments is investigated with Southern blots and by PCR to reveal whether insertions occurred in close vicinity. Clones where E1A and E1B 55K are present in single copy, or present in more than one copy but without inverted repeat conformation of these sequences in the genome of the transfected cells, or wherein E1A and at least one of the E1B coding sequences (in this case E1B-55K) are separated by at least 4 kb, preferably by at least 10 kb, more preferably by at least 34.5 kb, are preferably used further.

Example 2

Generation of Complementing Cell Lines Using Nucleic Acids that have E1A and E1B Regions Separated by Large Spacer Sequences As described in the previous example, it is possible to generate stably transformed cell clones from primary cells using separate plasmids for E1A and E1B. However, when DNA fragments are transfected together, there is still a chance that the transfected fragments end up in near proximity of each other, although this chance is reduced in the absence of considerable sequence overlap. The possibility of E1A and E1B expression cassette integration with less than 30 kb non-E1 sequence in between in the chromosome can be avoided by flanking the different E1 expression cassettes with large pieces of non-(E1-)coding DNA sequences (so called "spacer" fragments). If an E1A-carrying fragment integrates next to an E1B-containing fragment in the genome of the generated packaging cell, the large flanking sequences should create enough distance to eliminate the chance that the E1A and E1B encoding sequences recombine into the same recombinant vector molecule upon propagation of a recombinant adenoviral vector in the packaging cell. Non-limiting examples of large spacer DNA fragments that can be used are large sequences derived from, e.g., the human dystrophin gene or the human Apo-E1 gene. Other spacing molecules can also be used, even from non-human sources. Preferably, the flanking sequences do not contain coding regions for functional proteins and can thus be derived from intron sequences. Also, the E1A and E1B sequences do not need to be on different molecules but may be situated on the same large molecule, such as a cosmid. Examples of these E1A- and E1B-carrying molecules are given in FIG. 13. In preferred embodiments, the distance between the E1A and E1B coding regions is >34.5 kb because then co-insertion of the two regions into a virus results in a genome that is too large to be packaged. This situation will, for instance, be reached when two separate cosmid fragments of approximately 40 kb having the expression cassettes roughly in the middle are used. However, assuming that E1 in the form of inverted repeat structures contributes to the frequency of HDEP generation, then a construct where E1A and E1B cassettes are located on a single cosmid fragment of a total length of approximately 22 kb (like in FIG. 13, Panel I) suffices even when a second copy would become located in the genome of the cell in inverted orientation next to the first. Full integration of the mirror-imaged structure would then also involve a fragment of >38 kb. Also, if the presence of inverted repeats increases the frequency of HDEP formation, then a situation where multiple copies are integrated as direct repeats is considered less of a problem even when the DNA fragment that includes two full copies of E1A and E1B has a length of ≦20 kb. In the absence of inverted repeats, integration of any E1-containing fragment larger than the space left in the recombinant virus (i.e., 38 kb minus actual genome length of recombinant virus) into the recombinant virus forces it to delete parts of the essential viral sequences as a sequential step to ensure packaging and thus propagation. Analysis of the first HDEP genome that arose via homologous recombination (Murakami et al., 2002) showed that deletion of viral sequences is possible.

DNA sequences that integrate into the genome of a cell are not always accessible for activating transcription factors due to chromatin-associated repression. Especially when large fragments of intron DNA are used that originate from genomic regions that are normally not active in the cell that will be transduced with these sequences, gene expression may be shut-off due to inactive chromatin. Recently, sequences were identified that can inhibit this repression. Examples are the chicken β-globin HS4 element (U.S. Pat. No. 5,610,053) that functions as an insulator sequence, a *Drosophila* scs or scs' element (Kellum et al., 1991; Farkas et al., 1992), and a series of sequences in the human genome (so-called anti-repressor elements or STAR elements) identified by a specific screen for anti-repressor elements (Kwaks et al., 2003; WO 03/004704). Incorporation of such sequences in the E1A and E1B expression constructs, which sequences prevent positional silencing of the E1A and/or E1B genes, also enhances the amount of immortalized clones. Therefore, in certain embodiments of the present invention, one or more STAR-elements, for instance, STAR 7 (Genbank accession number AY190751) or STAR 40 (Genbank accession number AY190756), are present in at least one of the E1A and/or E1B expression constructs. Preferably, the elements are flanking both sides of the E1A and/or E1B coding sequences, i.e., the expression constructs may comprise from 5' to 3': STAR element—expression regulatory sequence (e.g., promoter)—E1A coding sequence; or E1A+one E1B coding sequence; or one E1B coding sequence; or both E1B coding sequences—polyadenylation sequence—STAR element.

Example 3

Generation of Cell Lines with E1A and E1B on Separate Constructs and Flanked by Stuffer DNA This example describes the generation of new cell lines according to the invention by co-transfection of a first DNA fragment having an E1A expression cassette flanked by large stuffer DNA and a second DNA fragment having an E1B expression cassette flanked by plasmid DNA.

Figure 17:
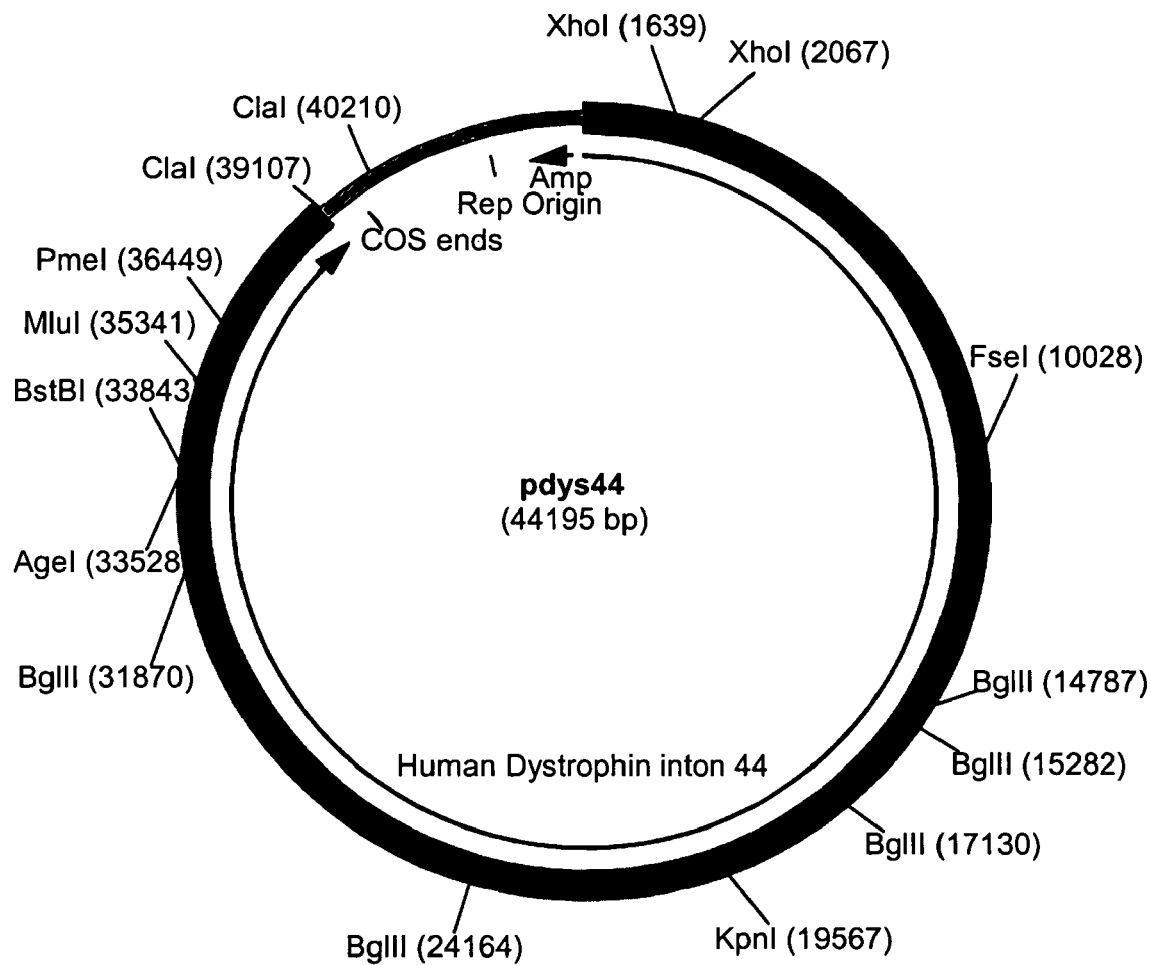
FIG. 17 is a map of pdys44.

The human dystrophin intron 44 sequence (Genbank Acc. No. M86524) cloned in a cosmid vector backbone (pdys44; FIG. 17) was taken in this example as a stuffer DNA surrounding the E1A expression plasmid.

Construct pCC.E1A (described in Example 1; FIG. 4) was digested with AflIII and AvrII (New England Biolabs) and protruding ends were made blunt with Klenow enzyme (New England Biolabs). Digested fragments were separated on a 0.5% TAE agarose gel and the 2 kb fragment corresponding to the PGK-E1A expression cassette was purified using the gel extraction kit (Qiagen) according to the manufacturer's description.

Figure 18:
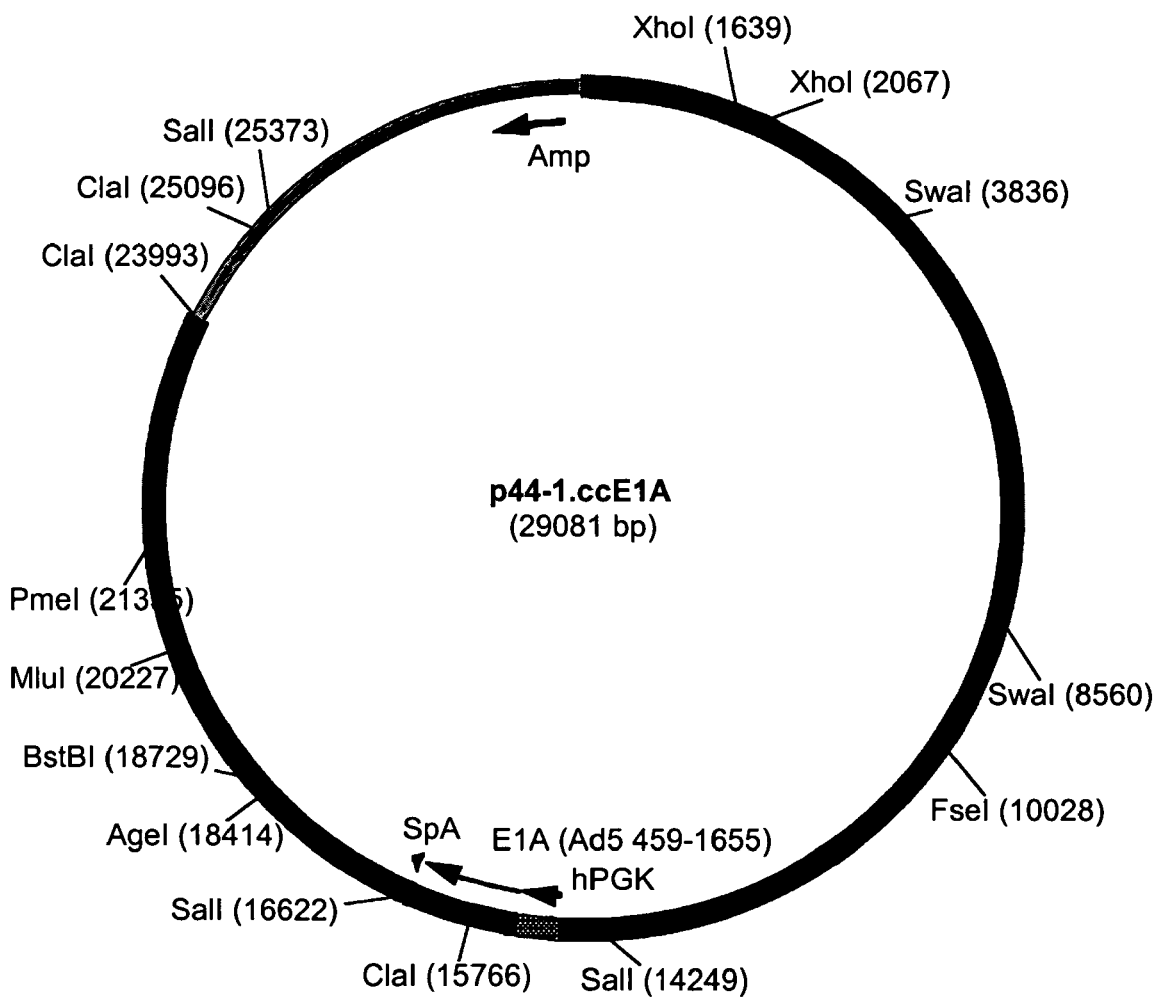
FIG. 18 depicts a map of p44-1.ccE1A.

The construct pdys44 (FIG. 17) was digested with BglII (New England Biolabs) and protruding ends were made blunt with Klenow enzyme. Fragments were separated on a 0.5% TAE agarose gel and the 27 kb fragment containing the backbone plasmid and part of the dystrophin intron was excised. The gel slice was then put in a syringe containing a bit of glass wool and, using the plunger, the buffer containing DNA was pushed in an Eppendorf tube. The thus obtained DNA solution contained approximately 5 ng/µl and was used directly in the ligation reaction with the purified 2 kb PGK-E1A fragment. Transformation into DH5αT1-competent cells resulted in construct p44-1.ccE1A (FIG. 18). The construct contains E1A under control of the human PGK promoter and a synthetic polyA signal.

Construct pE1B (described in Example 1; FIG. 3) was used in this example as the E1B expression plasmid. The plasmid contains E1B under control of its own promoter and a hepatitis B virus (HBV) polyA signal.

Construct p44-1.ccE1A was digested with XhoI and PmeI and digested DNA was purified by phenol/chloroform (1:1) extraction followed by Ethanol precipitation (resulting in E1A coding sequences flanked by a stuffer of about 11.6 kb upstream (including the PGK promoter) and about 6.5 kb downstream (including the synthetic polyA signal) of the E1A coding sequences). DNA was then pelleted, washed with 70% ethanol and aseptically dissolved in sterile endotoxin-free TE. Plasmid pE1B was digested with ScaI and purified as above (resulting in E1B coding sequences flanked by a stuffer of about 1.4 kb upstream and more than 2.3 kb downstream of the E1B coding sequences, the downstream stuffer including the HBV polyA sequence).

Primary human HER cells were cultured and transfected on passage number 6 (PN6) in one series of transfections and on PN9 in a second series of transfections. HER cell culture and transfections were done according to the method described in Example 1. The E1A- and E1B-containing DNAs prepared above were mixed in different proportions in separate transfections (both fragments lack significant overlap with respect to each other), derived from vector sequences or regulatory sequences, thereby reducing the chances of homologous recombination between the two fragments. If both fragments would form a single nucleic acid molecule (e.g., by end-to-end joining or ligation, a theoretical possibility) and subsequently integrate into the genome as a single unit, the E1A and E1B coding sequences in the resulting cells would be separated by more than 4 kb of stuffer sequences (at least 6.5 kb (downstream E1A)+1.4 kb (upstream E1B)=at least 7.9 kb between the E1A and E1B coding sequences, in theory). A total of eight dishes were transfected with approximate equimolar ratios of both constructs (17 µg E1A and 3 µg E1B plasmid) and three dishes were transfected with 10 µg of each fragment. Foci were observed in both series of transfections but in the case of 10 µg of each construct, relatively more foci were obtained. Construct pIG.E1A.E1B digested with AseI and BglI was used as a positive control (20 µg DNA/dish) on separate dishes. As expected, the efficiency of foci formation was higher with the (single) positive control plasmid than with the two separate fragments (from p44-1.ccE1A and pE1B). The pIG.E1A.E1B plasmid was approximately ten times more efficient. Still, both with the positive control plasmid and with the two-fragment transfection, about 80 to 90% of the transformed cell clones that were picked were found to be viable and established as a cell line.

These experiments clearly show that it is feasible to transform primary cells by co-transfection with E1A and E1B genes on separate DNA fragments and flanked by (non-overlapping) stuffer DNA. A total of six clones, HER01-B-71 (deposited on 1 Oct. 2004 at the European Collection of Cell Cultures (ECACC) under number 04100101), HER01-H-87 (deposited on 1 Oct. 2004 at the ECACC under number 04100102), HER01-H-86, HER01-H-88, HER01-H-89 and HER01-B-90, were analyzed further.

Expression of the E1 genes was analyzed using specific antibodies for the E1 proteins on Western Blots. A total amount of 10 µg protein from a lysate of the generated cell clones was used in the Western blot assay. The samples were denatured for 15 minutes at 70° C. after addition of ¼ volume NuPage sample buffer (Invitrogen). As a positive control, PER.C6® cell lysate was used. Untransfected primary HER cell lysate (passage number 6) served as a negative control. The samples were run on a 10% BisTris SDS page gel (Invitrogen), alongside a Seeblue plus2 prestained marker (Invitrogen). A Western blot was prepared from the gel. The following antibodies were used: either 1) E1A: mouse anti-human Ad2.E1A (1:400, Santa Cruz), or 2) E1B.19K: rat anti-human E1B 21K monoclonal (1:500, Oncogene), or 3) E1B.55K: mouse anti-human 55 Kda (harvested from hybridoma cell line C9A1C6, obtained from Dr. R. Hoeben, LUMC, Leiden). The following antibodies were used as a second antibody: 1) E1A: Goat-anti mouse IgG-HRP (Biorad), 2) E1B.19K: Goat-anti rat IgG-HRP (Epcam), 3) E1B.55K: µl Goat-anti mouse IgG-HRP (Biorad). The proteins were visualized by the use of an ECL+assay (Amersham).

Figure 19:
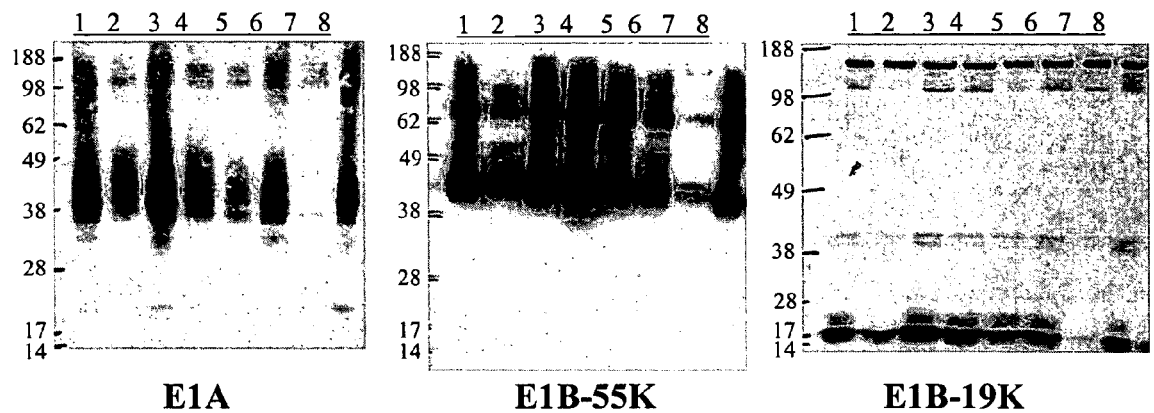
FIG. 19 depicts Western blots of protein lysates from generated cell lines. Lane 1, HER01-B-71; Lane 2, HER01-H-86; Lane 3, HER01-H-87; Lane 4, HER01-H-88; Lane 5, HER01-H-89; Lane 6, HER01-B-90; Lane 7, HER01 pn06 cells; and Lane 8, PER.C6 cells.

From these experiments, it is clear that all tested clones express E1A and E1B proteins and that the levels are comparable to those in PER.C6® cells (FIG. 19). This confirms that the transformation of the primary cells is indeed induced by Ad5 E1 expression and not the result of a spontaneous event.

Figure 20:
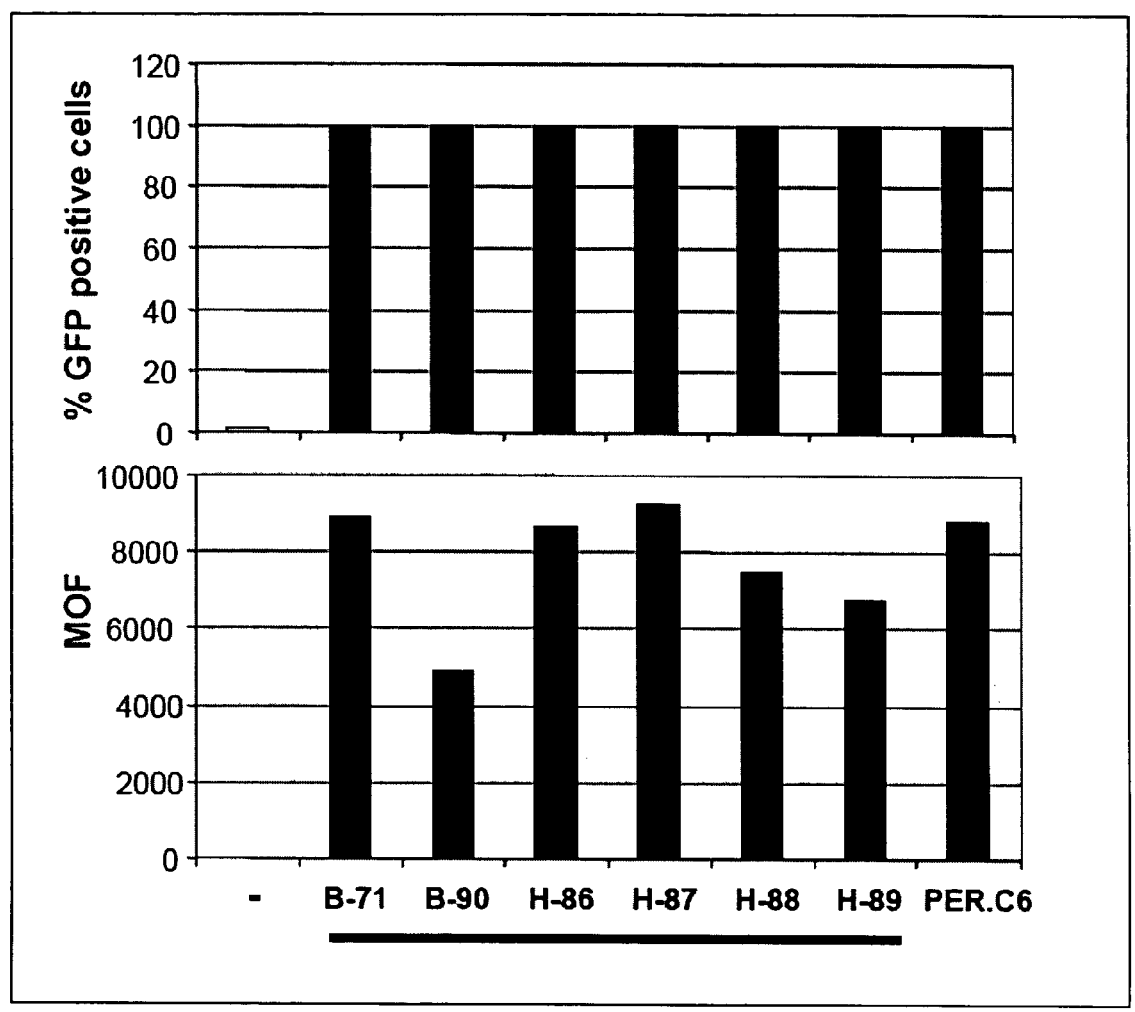
FIG. 20 is a demonstration of complementation of E1-deleted adenovirus vectors with transformed cell clones. −: negative control; MOF: mean of fluorescence; B-71, B-90, H-86, H-87, H-88, H-89: generated transformed cell clones.

Functional expression of Ad5 E1 genes in these cell lines can also be tested by showing that the cells are able to complement E1-deleted Ad5 viruses. Therefore, the six different cell clones were tested for replication of an Ad5.eGFP vector, an E1-deleted (deletion of nt. 455-3510 of the Ad5 sequence) Ad5-based adenovirus vector expressing Green Fluorescent Protein. Hereto, cells were seeded at a density of $1\times10^6$ cells/well and infected the day after with a multiplicity of infection (MOI) of five virus particles (VP)/cell. As a positive control, PER.C6® cells were also seeded and infected with an MOI of 5. Five days later, full cytopathogenic effect (CPE) was seen in all wells. Cells and medium were harvested, freeze/thawed three times and centrifuged to remove cell debris. Supernatants (crude lysates) were then used to infect A549 cells. Hereto, $5\times10^5$ A549 cells were seeded in 24-well plates and one day later infected with 50 µl of the crude lysates. Two days later, A549 cells were harvested and analyzed for GFP expression by FACS. Results show that all clones are able to complement an Ad5.eGFP vector (FIG. 20).

Notably, the adenovirus vector (E1-deleted, lacks nt 455-3510) has no overlap with the E1 sequences present in the cell line (Ad5 nt 459-3510) and, therefore, the combination of adenovirus vector with the new cell lines in this example amounts to a packaging system according to the invention, and the generation of recombinant adenovirus in this example amounts to a method of generating a batch of recombinant adenovirus according to the invention.

Figure 21:
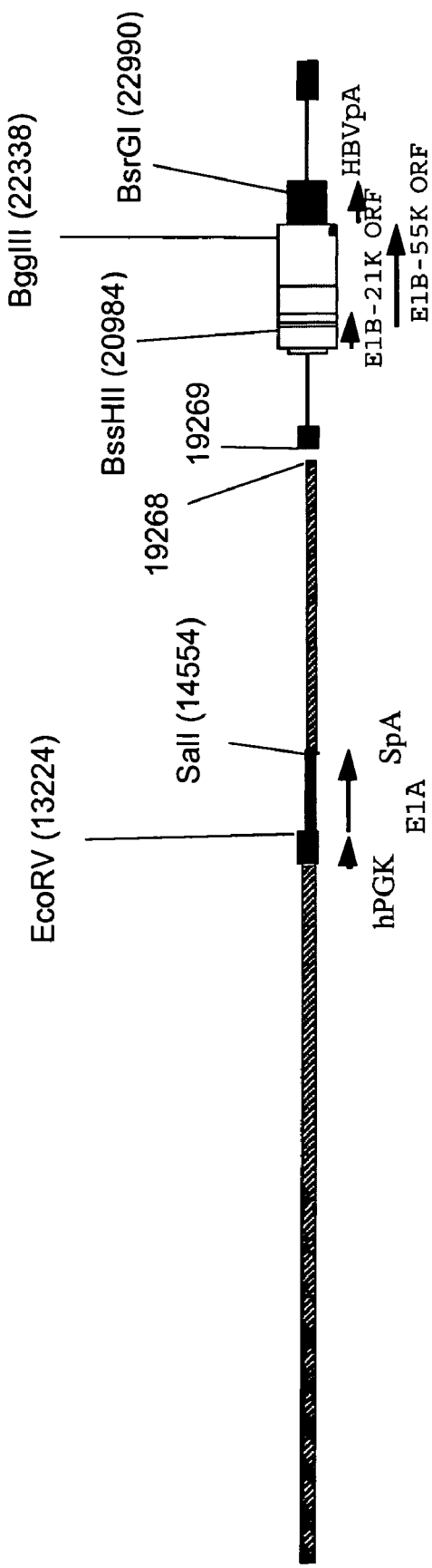
FIG. 21 is a schematic overview of the Ad5.E1 constructs used for the transfection in Example 3. The restriction sites used to digest the genomic DNA and to generate the probe fragments are indicated. The E1A and the E1B DNA fragment are fictively linked with nucleotide numbering starting at the 5' end of the E1A-containing fragment.

Genomic DNA from the generated cell lines is tested on Southern blots, using E1A and E1B probes, to demonstrate that the E1A and E1B coding sequences are separated by more than 4 kb in the genome of the cells. Hereto, the genomic DNA is digested with the restriction endonucleases EcoRV and BglII (FIG. 21). The digested DNA is size separated by gel electrophoresis (e.g., using field-inversed gel electrophoresis, FIGE, to enable separation of large DNA fragments) and then transferred to a nylon membrane by capillary blotting. Three different probes are radioactively labeled for hybridization of the blots. One Ad5.E1A probe is generated from an EcoRV-SalI restriction fragment (1330 bp; see FIG. 21) located 3' from the EcoRV site in the Ad5.E1A gene. Two Ad5.E1B probes are generated: Ad5.E1B(5'), from a BssHII-BglII fragment (1354 bp), and Ad5.E1B(3'), from a BglII-BsrGI fragment (652 bp), which are located at the 5' side and the 3' side of the BglII site in the Ad5.E1B gene, respectively. Identical blots containing the digested genomic DNA of the generated cell lines are prepared or, alternatively, the blot is stripped after hybridization of the first probe and then hybridized to a second. Either method should allow overlay of the signals obtained with E1A and the E1B probes.

If, following transfection and integration during generation of the transformed cell line, the E1A fragment becomes integrated next to an E1B-containing fragment, the probes for E1A and E1B detect the same bands on the blots, the size of the band identifying the distance between the two genes. Since the orientation of the E1A and E1B fragment relative to each other is not known, the two E1B probes are used separately, enabling hybridization either to the fragment 5' or 3' of the BglII restriction site. If an E1A fragment becomes integrated next to another E1A fragment, then the band resulting from EcoRV digestion will not be recognized by the E1B probe. Also, single integrants or end fragments will generate bands that are not recognized by both probes.

Altogether, the experiments in this example clearly show that co-transfection of primary human cells with separate plasmids, one containing E1A flanked by a large stuffer region and one containing E1B flanked by backbone sequences, results in transformed cell lines. Furthermore, these cell lines express E1 proteins in quantities sufficient for efficient complementation of E1-deleted Ad5 vectors.

In an alternative embodiment, the E1A and E1B sequences are cloned into a single construct, with a stuffer fragment between these sequences, after which cell lines are created using the single construct.

Clearly, if larger distances between E1A and E1B are desired, the E1B coding sequences may also be flanked by a longer stuffer nucleic acid, and/or the length of the stuffers flanking the E1A and E1B coding sequences could be increased, by standard routine molecular biology techniques, following the teachings of the present disclosure. Clearly, therefore, this example should not be construed to limit the scope of the invention to the actually performed experiments, but rather as an exemplification of the concepts of the present invention.

TABLE I

Transformation of primary HER cells with Ad5-E1 expression constructs

| Construct | Amount | # dishes | foci/dish |
|---|---|---|---|
| pIG.E1A.E1B | 20 µgr | 2 | 31 |
| pIG.E1A | 20 µgr | 2 | 0 |
| pIG.E1A + pE1B | 10 µgr each | 4 | 15 |
| pIG.E1AB21 | 20 µgr | 2 | 11.5 |
| pIG.E1AB21 + pE1B | 10 µgr each | 4 | 10 |
| AdApt.eGFP | 20 µgr | 1 | 0 |

REFERENCES

Byrd P., K. W. Brown, and P. H. Gallimore (1982). Malignant transformation of human embryo retinoblasts by cloned adenovirus 12 DNA. *Nature* 298:69-71.

Byrd P. J., R. J. A. Grand, and P. H. Gallimore (1988). Differential transformation of primary human embryo retinal cells by adenovirus E1 regions and combinations of E1A+ ras. *Oncogene* 2:477-484.

Fallaux F. J., A. Bout, I. van der Velde, D. J. M. van den Wollenberg, K. M. Hehir, J. Keegan, C. Auger, S. J. Cramer, H. van Ormondt, A. van der Eb, D. Valerio, and R. C. Hoeben (1998). New helper cells and matched early region 1-deleted adenovirus vectors prevent generation of replication-competent adenoviruses. *Hum. Gene Ther.* 9:1909-1917.

Farkas G. and A. Udvardy (1992). Sequence of scs and scs' *Drosophila* DNA fragments with boundary function in the control of gene expression. *Nucleic Acids Res.* 20:2604.

Gallimore P. H., P. J. Byrd, J. L. Whittaker, and R. J. A. Grand (1985). Properties of rat cells transformed by DNA plasmids containing adenovirus type 12 E1 DNA or specific fragments of the E1 region: comparison of transforming frequencies. *Cancer Res.* 45:2670-2680.

Gallimore P. H., R. J. A. Grand and P. J. Byrd (1986). Transformation of human embryo retinoblasts with simian virus 40, adenovirus and ras oncogenes. *Anti-Cancer Res.* 6:499-508.

Graham F. L., J. Smiley, W. C. Russell and R. Nairn (1977). Characteristics of a human cell line transformed by DNA from human adenovirus type 5. *J. Gen. Virol.* 36:59-72.

Jochemsen A. G., L. T. C. Peltenburg, M. F. W. te Pas, C. M. de Wit, J. L. Bos, A. J. van der Eb (1997). Activation of adenovirus 5 E1A transcription by region E1B in transformed primary rat cells. *EMBO. J.* 6:3399-3405.

Kwaks T. H., P. Barnett, W. Henrika, T. Siersma, R. G. Sewalt, D. J. Satijn, J. F. Brons, R. Van Blokland, P. Kwakman, A. L. Kruckeberg, A. Kelder, and A. P. Otte (2003). Identification of anti-repressor elements that confer high and stable protein production in mammalian cells. *Nature Biotech.* 21:553-558 (+corrigendum volume 21 number 7, July 2003, p. 822).

Kellum R. and P. Schedl (1991). A position-effect assay for boundaries of higher order chromosomal domains. *Cell* 64:941-950.

Lochmuller H., A. Jani, J. Huard, M. Prescott, M. Simoneau, B. Massie, G. Karpath and G. Acsadi (1994). Emergence of early region 1-containing replication-competent adenovirus in stocks of replication-defective adenovirus recombinants (dE1+dE3) during multiple passages in 293 cells. *Human Gene Therapy* 5:1485-1491.

Louis N., C. Evelegh and F. L. Graham (1997). Cloning and sequencing of the cellular-viral junctions from the human adenovirus type 5 transformed 293 cell line. *Virol.* 233: 423-429.

Murakami P., E. Pungor, J. Files, L. Do, R. van Rijnsoever, R. Vogels, A. Bout, M. McCaman (2002). A single short stretch of homology between adenoviral vector and packaging cell line can give rise to cytopathic effect-inducing, helper-dependent E1-positive particles. *Hum. Gene Ther.* 13:909-920.

Murakami P., M. Havenga, F. Fawaz, R. Vogels, G. Marzio, E. Pungor, J. Files, L. Do, J. Goudsmit, and M. McCaman (2004). Common structure of rare replication-deficient E1-positive particles in adenoviral vector batches. *J. Virol.* 78:6200-6208.

Nevels M., B. Tauber, T. Spruss, H. Wolf, and T. Dobner (2001). "Hit-and-Run" transformation by adenovirus oncogenes. *J. Virol.* 75:3089-3094.

Nichols W. W., R. Lardenoije, B. J. Ledwith, K. Brouwer, S. Manam, R. Vogels, D. Kaslow, D. Zuidgeest, A. J. Bett, L. Chen, M. van der Kaaden, S. M. Galloway, R. B. Hill, S. V. Machotka, C. A. Anderson, J. Lewis, D. Martinez, J. Lebron, C. Russo, D. Valerio, and A. Bout (2002). Propagation of adenoviral vectors: use of PER.C6 cells. In *Adenoviral vectors for gene therapy*, (Ed. D. T. Curiel and J. T. Douglas), Pub. Academic Press.

Rao L., M. Debbas, P. Sabbatini, D. Hockenbery, S. Korsmeyer and E. White (1992). The adenovirus E1A proteins induce apoptosis, which is inhibited by the E1B 19-kDa and Bcl-2 proteins. *Proc. Natl. Acad. Sci. USA* 89:7742-7746.

Steinwaerder D. S., C. A. Carlson, and A. Lieber (1999). Generation of adenovirus vectors devoid of all viral genes by recombination between inverted repeats. *J. Virol.* 73:9303-9313.

Van den Elsen P., S. de Pater, A. Houweling, J. van der Veer, and A. van der Eb (1982). The relationship between region E1a and E1b of human adenoviruses in cell transformation. *Gene* 18:175-185.

White E. (1995). Regulation of p53-dependent apoptosis by E1A and E1B. In: *The molecular repertoire of adenoviruses III*. Eds. W. Doerfler and P. Böhm, Springer-Verlag Berlin Heidelberg, 1995:33-58.

White E. (1996). Life, death, and the pursuit of apoptosis. *Genes Dev.* 10 (1):1-15.

Zantema A. and A. J. van der Eb (1995). Modulation of gene expression by adenovirus transformation. In: *The molecular repertoire of adenoviruses III*. Eds. W. Doerfler and P. Böhm, Springer-Verlag Berlin Heidelberg 1995:1-23.

---

What is claimed is:

1. A method of preparing a cell comprising an adenovirus E1A coding sequence, an adenovirus E1B-19K coding sequence, and an adenovirus E1B-55K coding sequence integrated into the cell's genome, the method comprising the step of introducing into a precursor cell a nucleic acid molecule or molecules selected from the group consisting of:
   a) a single nucleic acid molecule comprising said adenovirus E1A coding sequence, said adenovirus E1B-19K coding sequence, and said adenovirus E1B-55K coding sequence, wherein at least two of said adenovirus E1A coding sequence, said adenovirus E1B-19K coding sequence, and said adenovirus E1B-55K coding sequence are separated by at least 8 kb; and
   b) two or more nucleic acid molecules together comprising the E1A and E1B-19K and E1B-55K coding sequences wherein said E1A and at least one of the E1B coding sequences are separated by at least 8 kb when said two or more nucleic acid molecules would form a single molecule by end-to-end joining before integrating into the precursor cell's genome.

2. A method of preparing a cell comprising an adenovirus E1A coding sequence, an adenovirus E1B-19K coding sequence, and an adenovirus E1B-55K coding sequence integrated into the cell's genome, the method comprising: introducing into a precursor cell a nucleic acid molecule or molecules selected from the group consisting of:
   a) a single nucleic acid molecule comprising the adenovirus E1A coding sequence, the adenovirus E1B-19K coding sequence, and the adenovirus E1B-55K coding sequence, wherein at least two of said adenovirus E1A coding sequence, said adenovirus E1B-19K coding sequence, and said adenovirus E1B-55K coding sequence are separated by at least 10 kb; and
   b) two or more nucleic acid molecules together comprising the E1A and E1B-19K and E1B-55K coding sequences wherein said E1A and at least one of the E1B coding sequences are separated by at least 8 kb when said two or more nucleic acid molecules would form a single molecule by end-to-end joining before integrating into the precursor cell's genome.

3. The method according to claim 2, wherein at least two of said adenovirus E1A coding sequence, said adenovirus E1B-19K coding sequence, and said adenovirus E1B-55K coding sequence are separated by at least 34.5 kb.

4. A method of preparing a cell comprising an adenovirus E1A coding sequence, an adenovirus E1B-19K coding sequence, and an adenovirus E1B-55K coding sequence integrated into the cell's genome, the method comprising: introducing into a precursor cell a nucleic acid molecule or molecules selected from the group consisting of:
   a) a first nucleic acid molecule comprising the adenovirus E1A coding sequence and a separate second nucleic acid molecule comprising the adenovirus E1B-19K coding sequence and the adenovirus E1B-55K coding sequence, wherein the E1A coding sequence is under control of a first promoter and a first polyadenylation signal and wherein the E1B-19K and E1B-55K coding sequences are placed under control of a second promoter and a second polyadenylation signal and wherein the first promoter and second promoter are different and wherein the first and second polyadenylation signals are different, and wherein the first and second nucleic acid molecules have no substantial homologous sequence overlap able to result in homologous recombination between the first and second nucleic acid molecules;
   b) a single nucleic acid molecule comprising the adenovirus E1A coding sequence, the adenovirus E1B-19K coding sequence, and the adenovirus E1B-55K coding sequence, wherein at least two of the adenovirus E1A coding sequence, the adenovirus E1B-19K coding sequence, and the adenovirus E1B-55K coding sequence are separated by at least 4 kb; and b) two or more nucleic acid molecules together comprising the E1A and E1B-19K and E1B-55K coding sequences wherein said E1A and at least one of the E1B coding sequences are separated by at least 4 kb when said two or more nucleic acid molecules would form a single molecule by end-to-end joining before integrating into the precursor cell's genome, wherein, upon introduction into said precursor cell, said adenovirus E1B-55K coding sequence and said adenovirus E1B-19K coding sequence are on different nucleic acid molecules or said adenovirus E1B-55K coding sequence and said adenovirus E1B-19K coding sequence are on the same nucleic acid molecule and separated by at least 4 kb.

5. A recombinant molecule selected from the group consisting of a plasmid, cosmid, bacterial artificial chromosome, yeast artificial chromosome, and recombinants thereof generated by homologous recombination, ligation, site-specific recombination or end-to-end joining, the recombinant molecule comprising at least one nucleic acid sequence encoding an adenoviral E1A protein and at least one nucleic acid sequence encoding an adenoviral E1B protein, wherein said at least one nucleic acid sequence encoding said adenoviral E1A protein and at least one nucleic acid sequence encoding said adenoviral E1B protein are separated by at least 8 kb.

6. The recombinant molecule of claim 5, wherein said nucleic acid sequence encoding said adenoviral E1A protein and said nucleic acid sequence encoding said adenoviral E1B protein are separated by at least 10 kb.

7. The recombinant molecule of claim 6, wherein said nucleic acid sequence encoding said adenoviral E1A protein and said nucleic acid sequence encoding said adenoviral E1B protein are separated by at least 34.5 kb.

8. The recombinant molecule of claim 5, wherein said molecule is linear.

9. A set of at least two nucleic acid molecules comprising:
a) a first nucleic acid molecule selected from the group consisting of a plasmid, cosmid, bacterial artificial chromosome, and yeast artificial chromosome, said first nucleic acid molecule comprising an E1A coding sequence and encoding an adenovirus E1A protein, wherein said first nucleic acid molecule has at least 5 kb of spacer nucleic acid sequence on both sides of said E1A coding sequence, wherein said spacer nucleic acid molecule does not encode an adenovirus E1B protein; and
b) a second nucleic acid molecule selected from the group consisting of a plasmid, cosmid, bacterial artificial chromosome, and yeast artificial chromosome, said second nucleic acid molecule comprising an E1B coding sequence and encoding an adenovirus E1B protein, wherein said second nucleic acid molecule has at least 5 kb of spacer nucleic acid sequence on both sides of said E1B coding sequence, wherein said spacer nucleic acid does not encode an adenovirus E1A protein.

10. The set of at least two nucleic acid molecules of claim 9, wherein said spacer nucleic acid sequence is at least 17 kb.

11. A cell comprising the recombinant molecule of claim 5.

12. A cell comprising a set of at least two nucleic acid molecules of claim 9.

13. The cell of claim 11, wherein said recombinant molecule is integrated into the genome of said cell.

14. The cell of claim 12, wherein said at least two nucleic acid molecules are integrated into the genome of said cell.

15. The method according to claim 1, wherein the precursor cell is selected from the group consisting of retina cells, primary human retina cells, primary amniocytes, and primary human amniocytes.

16. The method according to claim 2, wherein the precursor cell is selected from the group consisting of retina cells, primary human retina cells, primary amniocytes, and primary human amniocytes.

17. The method according to claim 3, wherein the precursor cell is selected from the group consisting of retina cells, primary human retina cells, primary amniocytes, and primary human amniocytes.

18. The method according to claim 4, wherein the precursor cell is selected from the group consisting of retina cells, primary human retina cells, primary amniocytes, and primary human amniocytes.

* * * * *